(12) United States Patent
Farrell et al.

(10) Patent No.: US 6,610,312 B2
(45) Date of Patent: *Aug. 26, 2003

(54) COSMETIC EFFERVESCENT CLEANSING PILLOW

(75) Inventors: Linda Farrell, Stratford, CT (US); Craig Stephen Slavtcheff, Guilford, CT (US); Alexander Paul Znaiden, Trumbull, CT (US); Paul Vinski, Danbury, CT (US)

(73) Assignee: Unilever Home & Personal Care USA, Division of Conopco, Inc., Greenwich, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/783,777

(22) Filed: Feb. 15, 2001

(65) Prior Publication Data

US 2001/0026792 A1 Oct. 4, 2001

Related U.S. Application Data

(62) Division of application No. 09/532,767, filed on Mar. 22, 2000, now Pat. No. 6,217,854, which is a division of application No. 09/130,981, filed on Aug. 7, 1998, now Pat. No. 6,063,390.

(51) Int. Cl.[7] .............................. A61K 7/42; A61K 9/70; A61K 7/46; A61L 9/04; A01N 25/34

(52) U.S. Cl. .................................. 424/401; 424/43; 424/44; 424/59; 424/402; 424/404; 424/443; 512/4; 510/130; 510/135

(58) Field of Search ................... 424/401, 402, 424/404, 409, 443, 43, 44, 59; 512/4; 510/130, 135

(56) References Cited

U.S. PATENT DOCUMENTS

| 1,808,834 A | 6/1931 | Busch, Sr. |
|---|---|---|
| 3,242,093 A | 3/1966 | Compton et al. |
| 4,025,628 A | 5/1977 | Dewey et al. |
| 4,234,442 A | 11/1980 | Cornelissens |
| 4,272,393 A | 6/1981 | Gergely |
| 4,291,685 A | 9/1981 | Taelman |
| 4,311,606 A | 1/1982 | Kaeser |
| 4,515,703 A | 5/1985 | Haq |
| 4,592,855 A | 6/1986 | Gioffre et al. |
| 4,600,620 A | 7/1986 | Lloyd et al. |
| 4,601,938 A | 7/1986 | Deacon et al. |
| 4,603,069 A | 7/1986 | Haq et al. |
| 4,643,939 A | 2/1987 | Sugiyama et al. |
| 4,666,707 A | 5/1987 | Eguchi et al. |
| 4,745,021 A | 5/1988 | Ping, III et al. |
| 4,791,097 A | 12/1988 | Walele et al. |
| 4,808,322 A | 2/1989 | McLaughlin |
| 4,852,201 A | 8/1989 | Wundrock et al. |
| 4,886,387 A | 12/1989 | Goldberg et al. |
| 4,941,990 A | 7/1990 | McLaughlin |
| 5,006,339 A | 4/1991 | Bargery et al. |
| 5,026,551 A | 6/1991 | Yorozu et al. |
| 5,041,233 A | 8/1991 | Kutny et al. |
| 5,100,674 A | 3/1992 | Ser et al. |
| 5,198,198 A | 3/1993 | Gladfelter et al. |
| 5,306,439 A | 4/1994 | Lockhart |
| 5,338,476 A | 8/1994 | Pancheri et al. |
| 5,342,535 A | 8/1994 | Ramirez et al. |
| 5,352,387 A | 10/1994 | Rahman et al. |
| 5,431,841 A | 7/1995 | Lockhart |
| 5,560,873 A | 10/1996 | Chen et al. |
| 5,578,562 A | 11/1996 | Lockhart |
| 5,605,749 A | 2/1997 | Pike et al. |
| 5,607,681 A | 3/1997 | Galley et al. |
| 5,683,976 A | 11/1997 | Colurciello, Jr. et al. |
| 5,714,451 A | 2/1998 | Brouwer et al. |
| 5,718,729 A | 2/1998 | Harris |
| 5,720,949 A | 2/1998 | Davis |
| 5,804,546 A | 9/1998 | Hall |
| 5,955,057 A | 9/1999 | Maunder et al. |
| 6,063,390 A | 5/2000 | Farrell et al. |
| 6,093,218 A | 7/2000 | Hall et al. |
| 6,121,215 A | 9/2000 | Rau |

FOREIGN PATENT DOCUMENTS

| DE | 19745964 | 12/1996 |
|---|---|---|
| EP | 343070 | 5/1989 |
| EP | 343069 | 11/1989 |
| EP | 423015 | 4/1991 |
| EP | 0 806 201 | 5/1996 |
| GB | 2 118 961 | 4/1982 |
| JP | 62045519 | 2/1987 |
| JP | 10245075 | 9/1998 |
| WO | 97/43366 | 11/1997 |
| WO | 98/42303 | 10/1998 |

OTHER PUBLICATIONS

International Search Report, Oct. 11, 1999.

*Primary Examiner*—José G. Dees
*Assistant Examiner*—Marina Lamm
(74) *Attorney, Agent, or Firm*—Milton L. Honig

(57) ABSTRACT

A wiping article is provided which includes an effervescent cleanser composition held within a pouch formed from a first and second substrate sheet. At least one of the substrate sheets must be water permeable. The effervescent composition is an intimate mixture of an acid material such as citric acid and an alkaline material such as sodium bicarbonate. Water contact causes the combination to effervesce. A dry surfactant such as sodium cocoyl isethionate in contact with the water and effervescing carbon dioxide results in a highly pleasant sudsing system. Skin benefit agents may be included within the composition. The effervescent action may improve deposition of the skin benefit agents onto the skin.

4 Claims, No Drawings

US 6,610,312 B2

COSMETIC EFFERVESCENT CLEANSING PILLOW

This is a Divisional application of Ser. No. 09/532,767 filed Mar. 22, 2000 now U.S. Pat. No. 6,217,854, which is a Divisional application of Ser. No. 09/130,981, filed Aug. 7, 1998 now U.S. Pat. No. 6,063,390.

TECHNICAL FIELD

The present invention relates to a detergent composition comprising cationic and anionic surfactants and an acid and alkali source, which is suitable for use in laundry washing and dish washing methods.

BACKGROUND TO THE INVENTION

There is a trend amongst commercially available granular detergents towards higher bulk densities and towards granular detergent compositions which have a higher content of detergent active ingredients, such as various surfactants. Such detergents offer greater convenience to the consumer. The desire for such concentrated products ensures that the amount of filler materials are reduced and packaging materials which, ultimately, be disposed of.

Amongst consumers there is also a need for detergents which provide improved cleaning and stain removal. Therefore, in the recent past detergents have been developed which contain high levels of surfactant and various types of surfactants. Such as anionic, nonionic and cationic surfactants.

The high density detergents, comprising high levels of surfactants can lead to poor solubility properties, arising from low rate of dissolution or the formation of gels, and thus to poor dispensing of the product, either from the dispensing drawer of a washing machine, or from a dosing device placed with the laundry inside the machine. This poor dispensing is often caused by gelling of particles, which have high levels of surfactant, upon contact with water. The gel prevents a proportion of the detergent powder from being solubilized in the wash water which reduces the effectiveness of the powder. This is a particular problem at low water pressures and/or at lower washing temperatures.

WO94/28098 discloses a non-spray-dried detergent powder comprising a combination of an ethoxylated primary C8–18 alcohol, an alkali metal aluminosilicate builder and 5 to 40 wt % of a water-soluble salt of a citric acid.

EP-A-0 639 637 discloses the replacement of perborate bleach with an alkali metal percarbonate to improve the dispensing profile and dissolution rate of a detergent. Citrate or mixtures of citrate with sulphate or carbonate can be used to coat the percarbonate bleach. EP-A-0 639 639 contains a similar disclosure in this respect.

The use of effervescence to improve the dispensability of granular materials has been used extensively in pharmaceutical preparations. The most widely used effervescent system in this respect is citric acid in combination with bicarbonate. This effervescent system has also been described for improving the dispersibility of pesticidal compositions for controlling water-borne pests, e.g. GB-A-2,184,946.

EP-A-0 534 525 discloses the use of particulate citric acid with a specified particle size range of 350 to 1500 microns.

U.S. Pat. No. 5,114,647 discloses a sanitising composition comprising granules of alkali metal carbonate and aliphatic carboxylic acid of a particle size of 150 to 2,000 microns.

EP-A-0 333 223 discloses a bathing preparation comprising fumaric acid having an average particle size of 50–500 microns.

The addition of citric acid results in a reduction in alkalinity. However, an alkaline pH is required for an optimum performance of various detergent ingredients, such as certain surfactants. Overall an alkaline pH promotes cleaning, stain removal and soil suspension. Therefore, the incorporation of acids into detergent compositions is undesirable. For example, U.S. Pat. No. 4,414,130 discloses detergents, comprising organic acids, wherein certain compounds such as cationic surfactants are preferably omitted.

The Applicants now have found that the particular problems associated with dispensing a detergent composition comprising anionic and cationic surfactants can be improved by the inclusion of an acid and an alkali source whilst the performance of the cationic and anionic surfactants is maintained. This eliminates or reduces the problems of solid detergent particles remaining in the washing machine and on washed clothes.

Furthermore, since the surfactants are more efficiently dispensed into the wash water, the overall performance of the surfactants is more efficient and an overall improved cleaning, stain removal and soil suspending can be achieved.

Furthermore, the detergent residues in the dispensing drawer or dispensing device are reduced.

All documents cited in the present description are, in relevant part, incorporated herein by reference.

SUMMARY OF THE INVENTION

According to the present invention there is provided a detergent composition comprising an anionic surfactant, present at a level of from 0.5% to 60% by weight, a cationic surfactant, present at a level of from 0.01% to 30% by weight, and an acid source and an alkali source wherein said acid source and alkali source are capable of reacting together in the presence of water.

DETAILED DESCRIPTION OF THE INVENTION

The detergent composition of the present invention comprises four essential ingredients: anionic surfactant, cationic surfactant, an acid source and an alkali source. These and optional ingredients, and processes for making the detergents, are described in detail below.

Detergent Surfactants

The detergent composition can comprise one or more anionic surfactants, as described below, and one or more cationic surfactants.

Optionally, additional surfactants, selected from the group consisting of additional anionic and cationic surfactants, nonionic, zwitterionic, ampholytic and amphoteric surfactants can be present.

The total amount of surfactants is preferably of from 1% to 90%, preferably 3% to 70%, more preferably 5% to 40%, even more preferably 10% to 30%, most preferably 12% to 25% by weight of the detergent composition.

A preferred aspect of the present invention is a granular detergent composition. One or more of the surfactants can be comprised in a base composition, containing preferably also a builder material. The base composition may be prepared by spray-drying and dry-mixing/agglomeration. The base composition may also comprise some or all of the alkali source. Alternatively the acid source and/or alkali source may be added as separate components to the detergent base composition, preferably in a granular form.

Anionic Surfactant

The detergent composition of the present invention comprises one or more anionic surfactants. Any anionic surfactant useful for detersive purposes are suitable. Examples include salts (including, for example, sodium, potassium, ammonium, and substituted ammonium salts such as mono-, di- and triethanolamine salts) of the anionic sulfate, sulfonate, carboxylate and sarcosinate surfactants. Anionic sulfate surfactants are preferred.

Other anionic surfactants include the isethionates such as the acyl isethionates. N-acyl taurates, fatty acid amides of methyl tauride, alkyl succinates and sulfosuccinates, monoesters of sulfosuccinate (especially saturated and unsaturated $C_{12}$–$C_{18}$ monoesters) diesters of sulfosuccinate (especially saturated and unsaturated $C_6$–$C_{14}$ diesters), N-acyl sarcosinates. Resin acids and hydrogenated resin acids are also suitable, such as rosin, hydrogenated rosin, and resin acids and hydrogenated resin acids present in or derived from tallow oil.

The anionic surfactant is present at a level of 0.5% to 60%, preferably at a level of from 3% to 50%, more preferably of from 5% to 35%, most preferably from 65 to 20% by weight of the composition.

The ratio of the anionic surfactant to the cationic surfactant is preferably from 25:1 to 1:3, more preferably from 15:1 to 1:1, most preferably from 10:1 to 1:1.

Anionic Sulfate Surfactant

Anionic sulfate surfactants suitable for use herein include the linear and branched primary and secondary alkyl sulfates, alkyl ethoxysulfates, fatty oleoyl glycerol sulfates, alkyl phenol ethylene oxide ether sulfates, the $C_5$–$C_{17}$ acyl-N-($C_1$–$C_4$ alkyl) and —N—($C_1$–$C_2$ hydroxyalkyl) glucamine sulfates, and sulfates of alkylpolysaccharides such as the sulfates of alkylpolyglucoside (the nonionic nonsulfated compounds being described herein).

Alkyl sulfate surfactants are preferably selected from the linear and branched primary $C_9$–$C_{22}$ alkyl sulfates, more preferably the $C_{11}$–$C_{15}$ branched chain alkyl sulfates and the $C_{12}$–$C_{14}$ linear chain alkyl sulfates.

Alkyl ethoxysulfate surfactants are preferably selected from the group consisting of the $C_{10}$–$C_{18}$ alkyl sulfates which have been ethoxylated with from 0.5 to 20 moles of ethylene oxide per molecule. More preferably, the alkyl ethoxysulfate surfactant is a $C_{11}$–$C_{18}$, most preferably $C_{11}$–$C_{15}$ alkyl sulfate which has been ethoxylated with from 0.5 to 7, preferably from 1 to 5, moles of ethylene oxide per molecule.

A particularly preferred aspect of the invention employs mixtures of the preferred alkyl sulfate and alkyl ethoxysulfate surfactants. Such mixtures have been disclosed in PCT Patent Application No. WO 93/18124.

Anionic Sulfonate Surfactant

Anionic sulfonate surfactants suitable for use herein include the salts of $C_5$–$C_{20}$ linear alkylbenzene sulfonates, alkyl ester sulfonates, $C_6$–$C_{22}$ primary or secondary alkane sulfonates, $C_6$–$C_{24}$ olefin sulfonates, sulfonated polycarboxylic acids, alkyl glycerol sulfonates, fatty acyl glycerol sulfonates, fatty oleyl glycerol sulfonates, and any mixtures thereof.

Anionic Carboxylate Surfactant

Suitable anionic carboxylate surfactants include the alkyl ethoxy carboxylates, the alkyl polyethoxy polycarboxylate surfactants and the soaps ('alkyl carboxyls'), especially certain secondary soaps as described herein.

Suitable alkyl ethoxy carboxylates include those with the formula $RO(CH_2CH_2O)_x CH_2COO^-M^+$ wherein R is a $C_6$ to $C_{18}$ alkyl group, x ranges from 0 to 10, and the ethoxylate distribution is such that, on a weight basis, the amount of material where x is 0 is less than 20% and M is a cation. Suitable alkyl polyethoxy polycarboxylate surfactants include those having the formula $RO$—$(CHR_1$—$CHR_2$—$O)_x$—$R_3$ wherein R is a $C_6$ to $C_{18}$ alkyl group, x is from 1 to 25, $R_1$ and $R_2$ are selected from the group consisting of hydrogen, methyl acid radical, succinic acid radical, hydroxysuccinic acid radical, and mixtures thereof, and $R_3$ is selected from the group consisting of hydrogen, substituted or unsubstituted hydrocarbon having between 1 and 8 carbon atoms, and mixtures thereof.

Suitable soap surfactants include the secondary soap surfactants which contain a carboxyl unit connected to a secondary carbon. Preferred secondary soap surfactants for use herein are water-soluble members selected from the group consisting of the water-soluble salts of 2-methyl-1-undecanoic acid, 2-ethyl-1-decanoic acid, 2-propyl-1-nonanoic acid, 2-butyl-1-octanoic acid and 2-pentyl-1-heptanoic acid. Certain soaps may also be included as suds suppressors.

Alkali Metal Sarcosinate Surfactant

Other suitable anionic surfactants are the alkali metal sarcosinates of formula R-CON ($R^1$) $CH_2$ COOM, wherein R is a $C_5$–$C_{17}$ linear or branched alkyl or alkenyl group, $R^1$ is a $C_1$–$C_4$ alkyl group and M is an alkali metal ion. Preferred examples are the myristyl and oleoyl methyl sarcosinates in the form of their sodium salts.

Cationic Surfactant

Another essential component of the detergent composition of the invention is a cationic surfactant, present at a level of from 0.1% to 30% by weight of the detegent composition. The cationic surfactant is preferably present at a level of from 0.1% to 20%, more preferably from 0.4% to 7%, most preferably from 0.5% to 3% by weight of the detergent composition.

The ratio of the anionic surfactant to the cationic surfactant is preferably from 25:1 to 1:3, more preferably from 15:1 to 1:1. most preferably from 10:1 to 1:1.

Preferably the cationic surfactant is selected from the group consisting of cationic ester surfactants, cationic mono-alkoxylated amine surfactants, cationic bis-alkoxylated amine surfactants and mixtures thereof.

Cationic Ester Surfactant

The cationic surfactant may comprise a cationic ester surfactant.

If present in the detergent composition of the invention, the cationic ester surfactant is preferably present at a level from 0.1% to 20.0%, more preferably from 0.4% to 7%, most preferably from 0.5% to 3.0% by weight of the detergent composition.

The cationic ester surfactant is preferably a water dispersible compound having surfactant properties comprising at least one ester (i.e. —COO—) linkage and at least one cationically charged group.

Suitable cationic ester surfactants, including choline ester surfactants, have for example been disclosed in U.S. Pat. Nos. 4,228,042, 4,239,660 and 4,260,529.

In one preferred aspect the ester linkage and cationically charged group are separated from each other in the surfactant molecule by a spacer group consisting of a chain comprising at least three atoms (i.e. of three atoms chain length), preferably from three to eight atoms, more preferably from three to five atoms, most preferably three atoms. The atoms forming the spacer group chain are selected from the group consisting of carbon, nitrogen and oxygen atoms and any mixtures thereof, with the proviso that any nitrogen or oxygen atom in said chain connects only with carbon atoms in the chain. Thus spacer groups having, for example, —O—O— (i.e. peroxide), —N—N—, and —N—O— linkages are excluded, whilst spacer groups having, for example —CH$_2$—O—CH$_2$— and —CH$_2$—NH—CH$_2$— linkages are included. In a preferred aspect the spacer group chain comprises only carbon atoms, most preferably the chain is a hydrocarbyl chain.

Preferred cationic ester surfactants are those having the formula:

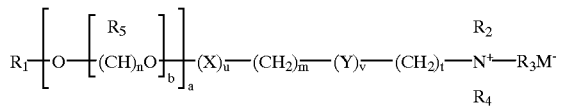

wherein R$_1$ is a C$_5$–C$_{31}$ linear or branched alkyl, alkenyl or alkaryl chain or M$^-$. N$^+$(R$_6$R$_7$R$_8$)(CH$_2$)$_s$; X and Y, independently, are selected from the group consisting of COO, OCO, O, CO, OCOO, CONH, NHCO, OCONH and NHCOO wherein at least one of X or Y is a COO, OCO, OCOO, OCONH or NHCOO group; R$_2$, R$_3$, R$_4$, R$_6$, R$_7$, and R$_8$ are independently selected from the group consisting of alkyl, alkenyl, hydroxyalkyl and hydroxy-alkenyl groups having from 1 to 4 carbon atoms and alkaryl groups; and R$_5$ is independently H or a C$_1$–C$_3$ alkyl group; wherein the values of m, n, s and t independently lie in the range of from 0 to 8, the value of b lies in the range from 0 to 20, and the values of a, u and v independently are either 0 or 1 with the proviso that at least one of u or v must be 1; and wherein M is a counter anion.

Preferably M is selected from the group consisting of halide, methyl sulfate, sulfate, and nitrate, more preferably methyl sulfate, chloride, bromide or iodide.

In a preferred aspect, the cationic ester surfactant is selected from those having the formula:

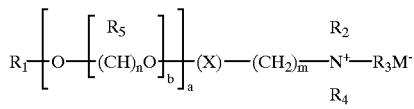

wherein R$_1$ is a C$_5$–C$_{31}$ linear or branched alkyl, alkenyl or alkaryl chain; X is selected from the group consisting of COO, OCO, OCOO, OCONH and NHCOO; R$_2$, R$_3$, and R$_4$ are independently selected from the group consisting of alkyl and hydroxyalkyl groups having from 1 to 4 carbon atoms; and R$_5$ is independently H or a C$_1$–C$_3$ alkyl group: wherein the value of n lies in the range of from 0 to 8, the value of b lies in the range from 0 to 20, the value of a is either 0 or 1, and the value of m is from 3 to 8.

More preferably R$_2$, R$_3$ and R$_4$ are independently selected from a C$_1$–C$_4$ alkyl group and a C$_1$–C$_4$ hydroxyalkyl group. In one preferred aspect at least one, preferably only one, of R$_2$, R$_3$ and R$_4$ is a hydroxyalkyl group. The hydroxyalkyl preferably has from 1 to 4 carbon atoms, more preferably 2 or 3 carbon atoms, most preferably 2 carbon atoms. In another preferred aspect at least one of R$_2$, R$_3$ and R$_4$ is a C$_2$–C$_3$ alkyl group, more preferably two C$_2$–C$_3$ alkyl groups are present.

In a preferred aspect two of R$_2$, R$_3$ and R$_4$ and the nitrogen of the cationically charged group from part of a ring structure. Preferably, the ring structure contains another nitrogen atom or more preferably, an oxygen atom, or mixtures thereof. Preferably, the ring structure contains 5 to 8 atoms, most preferably 6 atoms.

In a highly preferred aspect two of R$_2$, R$_3$ and R$_4$ and the nitrogen of the cationically charged group from part of a morpholino ring structure or a substituted morpholino ring structure. Highly preferred cationic ester surfactants of this ype are the esters having the formula:

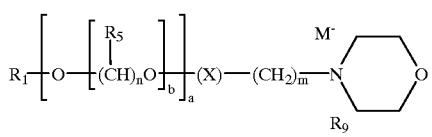

wherein R$_1$ is a C$_5$–C$_{31}$ linear or branched alkyl, alkenyl or alkaryl chain; X is selected from the group consisting of COO, OCO, OCOO, OCONH and NHCOO, R$_9$ is selected from the group consisting of alkyl, alkenyl, hydroxyalkyl and hydroxy-alkenyl groups having from 1 to 4 carbon atoms and alkaryl groups; and R$_5$ is independently H or a C$_1$–C$_3$ alkyl group; wherein the value of n lies in the range of from 0 to 8. the value of b lies in the range from 0 to 20, the value of a is either 0 or 1, and the value of m is from 3 to 8.

More preferably R$_2$, R$_3$ and R$_4$ are independently selected from a C$_1$–C$_4$ alkyl group and a C$_1$–C$_4$ hydroxyalkyl group. In one preferred aspect at least one, preferably only one, of R$_2$, R$_3$ and R$_4$ is a hydroxyalkyl group. The hydroxyalkyl preferably has from 1 to 4 carbon atoms, more preferably 2 or 3 carbon atoms, most preferably 2 carbon atoms. In another preferred aspect at least one of R$_2$, R$_3$ and R$_4$ is a C$_2$–C$_3$ alkyl group, more preferably two C$_2$–C$_3$ alkyl groups are present.

Highly preferred water dispersible cationic ester surfactants are the esters having the formula:

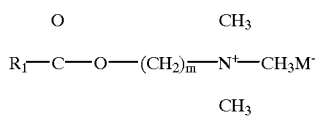

where m is from 1 to 4, preferably 2 or 3 and wherein R$_1$ is a C$_{11}$–C$_{19}$ linear or branched alkyl chain.

Particularly preferred choline esters of this type include the stearoyl choline ester quaternary methylammonium halides (R$^1$=C$_{17}$ alkyl), palmitoyl choline ester quaternary methylammonium halides (R$^1$=C$_{15}$ alkyl), myristoyl choline ester quaternary methylammonium halides (R$^1$=C$_{13}$ alkyl), lauroyl choline ester methylammonium halides (R$^1$=C$_{11}$ alkyl), cocoyl choline ester quaternary methylammonium halides (R$^1$=C$_{11}$–C$_{13}$ alkyl), tallowyl choline ester quaternary methylammonium halides (R$^1$=C$_{15}$–C$_{17}$ alkyl), and any mixtures thereof.

Other suitable cationic ester surfactants have the structural formulas below, wherein d may be from 0 to 20.

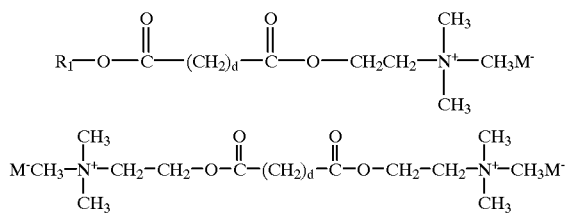

In a preferred aspect the cationic ester surfactant is hydrolysable under the conditions of a laundry wash method.

The particularly preferred choline esters, given above, may be prepared by the direct esterification of a fatty acid of the desired chain length with dimethylaminoethanol, in the presence of an acid catalyst. The reaction product is then quaternized with a methyl halide, preferably in the presence of a solvent such as ethanol, water, propylene glycol or preferably a fatty alcohol ethoxylate such as $C_{10}$–$C_{18}$ fatty alcohol ethoxylate having a degree of ethoxylation of from 3 to 50 ethoxy groups per mole forming the desired cationic material. They may also be prepared by the direct esterification of a long chain fatty acid of the desired chain length together with 2-haloethanol, in the presence of an acid catalyst material. The reaction product is then quaternized with trimethylamine, forming the desired cationic material.

Cationic Mono-Alkoxylated Amine Surfactants

The cationic surfactant of the present invention can contain a cationic mono-alkoxylated amine surfactant, which has the general formula:

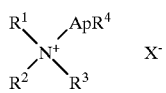

wherein $R^1$ is an alkyl or alkenyl moiety containing from about 6 to about 18 carbon atoms, preferably 6 to about 16 carbon atoms, most preferably from about 6 to about 11 carbon atoms; $R^2$ and $R^3$ are each independently alkyl groups containing from one to about three carbon atoms, preferably methyl; $R^4$ is selected from hydrogen (preferred), methyl and ethyl, $X^-$ is an anion such as chloride, bromide, methylsulfate, sulfate, or the like, to provide electrical neutrality; A is selected from $C_1$–$C_4$ alkoxy, especially ethoxy (i.e., —$CH_2CH_2O$—), propoxy, butoxy and mixtures thereof; and p is from 1 to about 30, preferably 1 to about 15, most preferably 1 to about 8.

Highly preferred cationic mono-alkoxylated amine surfactants for use herein are of the formula

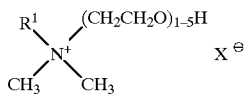

wherein $R^1$ is $C_6$–$C_{18}$ hydrocarbyl and mixtures thereof, preferably $C_6$–$C_{14}$, especially $C_6$–$C_{11}$ alkyl, preferably $C_8$ and $C_{10}$ alkyl, and X is any convenient anion to provide charge balance, preferably chloride or bromide.

As noted, compounds of the foregoing type include those wherein the ethoxy ($CH_2CH_2O$) units (EO) are replaced by butoxy, isopropoxy [$CH(CH_3)CH_2O$] and [$CH_2CH(CH_3)O$] units (i-Pr) or n-propoxy units (Pr), or mixtures of EO and/or Pr and/or i-Pr units.

When used in granular detergent compositions cationic mono-alkoxylated amine surfactants wherein the hydrocarbyl substituent $R^1$ is $C_6$–$C_{11}$, especially $C_{10}$, are preferred, because they enhance the rate of dissolution of laundry granules, especially under cold water conditions, as compared with the higher chain length materials.

The levels of the cationic mono-alkoxylated amine surfactants used in detergent compositions of the invention can range from 0.1% to 20%, more preferably from 0.4% to 7%, most preferably from 0.5% to 3.0% by weight of the composition.

Cationic Bis-Alkoxylated Amine Surfactant

The cationic surfactant of the invention can be a cationic bis-alkoxylated amine surfactant, which has the general formula:

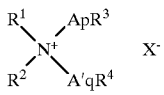

wherein $R^1$ is an alkyl or alkenyl moiety containing from about 6 to about 18 carbon atoms, preferably 6 to about 16 carbon atoms, more preferably 6 to about 11, most preferably from about 8 to about 10 carbon atoms; $R^2$ is an alkyl group containing from one to three carbon atoms, preferably methyl; $R^3$ and $R^4$ can vary independently and are selected from hydrogen (preferred), methyl and ethyl, $X^-$ is an anion such as chloride, bromide, methylsulfate, sulfate, or the like, sufficient to provide electrical neutrality. A and A' can vary independently and are each selected from $C_1$–$C_4$ alkoxy, especially ethoxy, (i.e., —$CH_2CH_2O$—), propoxy, butoxy and mixtures thereof; p is from 1 to about 30, preferably 1 to about 4 and q is from 1 to about 30, preferably 1 to about 4, and most preferably both p and q are 1.

Highly preferred cationic bis-alkoxylated amine surfactants for use herein are of the formula

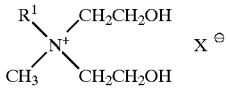

wherein $R^1$ is $C_6$–$C_{18}$ hydrocarbyl and mixtures thereof, preferably $C_6$, $C_8$, $C_{10}$, $C_{12}$, $C_{14}$ alkyl and mixtures thereof. X is any convenient anion to provide charge balance, preferably chloride. With reference to the general cationic bis-alkoxylated amine structure noted above, since in a preferred compound $R^1$ is derived from (coconut) $C_{12}$–$C_{14}$ alkyl fraction fatty acids, $R^2$ is methyl and ApR$^3$ and A'qR$^4$ are each monoethoxy.

Other cationic bis-alkoxylated amine surfactants useful herein include compounds of the formula:

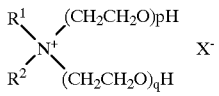

wherein $R^1$ is $C_6$–$C_{18}$ hydrocarbyl, preferably $C_6$–$C_{14}$ alkyl, independently p is 1 to about 3 and q is 1 to about 3, $R^2$ is $C_1$–$C_3$ alkyl, preferably methyl, and X is an anion, especially chloride or bromide.

Other compounds of the foregoing type include those wherein the ethoxy ($CH_2CH_2O$) units (EO) are replaced by butoxy (Bu) isopropoxy [$CH(CH_3)CH_2O$] and [$CH_2CH(CH_3)O$] units (i-Pr) or n-propoxy units (Pr), or mixtures of EO and/or Pr and/or i-Pr units.

When used in granular detergent compositions in accord with the invention, cationic bis alkoxylated amine surfactants wherein the hydrocarbyl substituent $R^1$ is $C_6$–$C_{11}$, especially $C_8$ or $C_{10}$, are preferred cationic surfactants, because they enhance the rate of dissolution of laundry granules, especially under cold water conditions, as compared with the higher chain length materials The levels of the cationic bis-alkoxylated amine surfactants used in detergent compositions of the invention can range from 0.1% to 20%, preferably from 0.4% to 7%, most preferably from 0.5% to about 3.0%, by weight of the detergent composition.

Alkali Source

In accordance with the present invention, an alkali source is present in the detergent composition such that it has the capacity to react with the source of acidity in the presence of water to produce a gas. Preferably this gas is carbon dioxide, and therefore the alkali is a carbonate, or a suitable derivative thereof.

The detergent composition of the present invention preferably contains from about 2% to about 75%, preferably from about 5% to about 60%, most preferably from about 10% to about 30% by weight of the alkali source. When the alkali source is present in an agglomerated detergent particle, the agglomerate preferably contains from about 10% to about 60% of the alkali source.

In a preferred embodiment, the alkali source is a carbonate. Examples of preferred carbonates are the alkaline earth and alkali metal carbonates, including sodium carbonate, bicarbonate and sesqui-carbonate and any mixtures thereof with ultra-fine calcium carbonate such as are disclosed in German Patent Application No. 2,321,001 published on Nov. 15, 1973. Alkali metal percarbonate salts are also suitable sources of carbonate species and are described in more detail in the section 'inorganic perhydrate salts' herein.

The alkali source may also comprise other components, such as a silicate. Suitable silicates include the water soluble sodium silicates with an $SiO_2:Na_2O$ ratio of from 1.0 to 2.8, with ratios of from 1.6 to 2.0 being preferred, and 2.0 ratio being most preferred. The silicates may be in the form of either the anhydrous salt or a hydrated salt. Sodium silicate with an $SiO_2:Na_2O$ ratio of 2.0 is the most preferred silicate. Alkali metal persilicates are also suitable sources of silicate herein.

Other suitable sources will be known to those skilled in the art.

Acid Source

In accordance with the present invention, the acid source is present in the detergent composition such that the it is capable of reacting with the source of alkali in the presence of water to produce a gas.

The acid source is preferably present at a level of from 0.1% to 50%, more preferably from 0.5% to 25%, even more preferably from 1% to 12%, even more preferably from 1% to 7%, most preferably from 2% to 5% by weight of the composition. In a preferred embodiment of the present invention the source of acidity is present in the range of about 1% to about 3%, most preferably about 3% by weight of the composition.

Preferably, 80% or more of the acid source has a particle size in the range of from about 150 microns to about 710 microns, with preferably at least about 37% by weight of the acid source having a particle size of about 350 microns or less. Preferably, 100% of the acid source has a particle size of about 710 microns or less, but this is not essential provided the aforementioned criteria are fulfilled. Alternatively, greater than about 38%, more preferably 38.7%, of the particulate acid source has a particle size of about 350 microns or less.

The particle size of the source of acidity is calculated by sieving a sample of the source of acidity on a series of Tyler sieves. For example, a Tyler seive mesh 100 corresponds to an aperture size of 150 microns. The weight fractions thereby obtained are plotted against the aperture size of the sieves.

The acid source may be any suitable organic, mineral or inorganic acid, or a derivative thereof, or a mixture thereof. The acid source may be a mono-, bi- or tri-protonic acid. Preferred derivatives include a salt or ester of the acid. The source of acidity is preferably non-hygroscopic, which can improve storage stability. However, a monohydrate acidic source can be useful herein. Organic acids and their derivatives are preferred. The acid is preferably water-soluble. Suitable acids include citric, glutaric, tartaric acid, succinic or adipic acid, monosodium phosphate, sodium hydrogen sulfate, boric acid, or a salt or an ester thereof. Citric acid is especially preferred.

Additional Detergent Components

The detergent compositions of the invention may also contain additional detergent components. The precise nature of these additional components, and levels of incorporation thereof will depend on the physical form of the composition, and the precise nature of the washing operation for which it is to be used.

The compositions of the invention preferably contain one or more additional detergent components selected from additional surfactants, bleaches, builders, organic polymeric compounds, enzymes, suds suppressors, lime soap dispersants, soil suspension and anti-redeposition agents and corrosion inhibitors.

Alkoxylated Nonionic Surfactant

Essentially any alkoxylated nonionic surfactants are suitable herein. The ethoxylated and propoxylated nonionic surfactants are preferred.

Preferred alkoxylated surfactants can be selected from the classes of the nonionic condensates of alkyl phenols, nonionic ethoxylated alcohols, nonionic ethoxylated/propoxylated fatty alcohols, nonionic ethoxylate/propoxylate condensates with propylene glycol, and the nonionic ethoxylate condensation products with propylene oxide/ethylene diamine adducts.

Nonionic Alkoxylated Alcohol Surfactant

The condensation products of aliphatic alcohols with from 1 to 25 moles of alkylene oxide, particularly ethylene oxide and/or propylene oxide, are suitable for use herein. The alkyl chain of the aliphatic alcohol can either be straight or branched, primary or secondary, and generally contains from 6 to 22 carbon atoms. Particularly preferred are the condensation products of alcohols having an alkyl group containing from 8 to 20 carbon atoms with from 2 to 10 moles of ethylene oxide per mole of alcohol.

Nonionic Polyhydroxy Fatty Acid Amide Surfactant

Polyhydroxy fatty acid amides suitable for use herein are those having the structural formula $R^2CONR^1Z$ wherein: R1 is H, $C_1$–$C_4$ hydrocarbyl, 2-hydroxy ethyl, 2-hydroxy propyl, ethoxy, propoxy, or a mixture thereof, preferable C1–C4 alkyl, more preferably $C_1$ or $C_2$ alkyl, most preferably $C_1$ alkyl (i.e., methyl); and $R_2$ is a $C_5$–$C_{31}$ hydrocarbyl, preferably straight-chain $C_5$–$C_{19}$ alkyl or alkenyl, more preferably straight-chain $C_9$–$C_{17}$ alkyl or alkenyl, most preferably straight-chain $C_{11}$–$C_{17}$ alkyl or alkenyl, or mixture thereof; and Z is a polyhydroxyhydrocarbyl having a linear hydrocarbyl chain with at least 3 hydroxyls directly connected to the chain, or an alkoxylated derivative (preferably ethoxylated or propoxylated) thereof. Z preferably will be derived from a reducing sugar in a reductive amination reaction; more preferably Z is a glycityl.

Nonionic Fatty Acid Amide Surfactant

Suitable fatty acid amide surfactants include those having the formula: $R^6CON(R^7)_2$ wherein $R^6$ is an alkyl group containing from 7 to 21, preferably from 9 to 17 carbon atoms and each $R^7$ is selected from the group consisting of hydrogen, $C_1$–$C_4$ alkyl, $C_1$–$C_4$ hydroxyalkyl, and —$(C_2H_4O)_xH$, where x is in the range of from 1 to 3.

Nonionic Alkylpolysaccharide Surfactant

Suitable alkylpolysaccharides for use herein are disclosed in U.S. Pat. No. 4,565,647, Llenado, issued Jan. 21, 1986, having a hydrophobic group containing from 6 to 30 carbon atoms and a polysaccharide, e.g., a polyglycoside, hydrophilic group containing from 1.3 to 10 saccharide units.

Preferred alkylpolyglycosides have the formula $$R^2O(C_nH_{2n}O)t(glycosyl)_x$$

wherein $R^2$ is selected from the group consisting of alkyl, alkylphenyl, hydroxyalkyl, hydroxyalkylphenyl, and mixtures thereof in which the alkyl groups contain from 10 to 18 carbon atoms; n is 2 or 3; t is from 0 to 10, and x is from 1.3 to 8. The glycosyl is preferably derived from glucose.

Amphoteric Surfactant

Suitable amphoteric surfactants for use herein include the amine oxide surfactants and the alkyl amphocarboxylic acids.

Suitable amine oxides include those compounds having the formula $R^3(OR^4)_xN^0(R^5)_2$ wherein $R^3$ is selected from an alkyl, hydroxyalkyl, acylamidopropoyl and alkyl phenyl group, or mixtures thereof, containing from 8 to 26 carbon atoms; $R^4$ is an alkylene or hydroxyalkylene group containing from 2 to 3 carbon atoms, or mixtures thereof; x is from 0 to 5, preferably from 0 to 3; and each $R^5$ is an alkyl or hydroxyalkyl group containing from 1 to 3, or a polyethylene oxide group containing from 1 to 3 ethylene oxide groups. Preferred are $C_{10}$–$C_{18}$ alkyl dimethylamine oxide, and $C_{10-18}$ acylamido alkyl dimethylanine oxide.

A suitable example of an aklyl aphodicarboxylic acid is Miranol(TM) C2M Conc. manufactured by Miranol, Inc., Dayton, N.J.

Zwitterionic Surfactant

Zwitterionic surfactants can also be incorporated into the detergent compositions or components thereof in accord with the invention. These surfactants can be broadly described as derivatives of secondary and tertiary amines, derivatives of heterocyclic secondary and tertiary amines, or derivatives of quaternary ammonium, quaternary phosphonium or tertiary sulfonium compounds. Betaine and sultaine surfactants are exemplary zwitterionic surfactants for use herein.

Suitable betaines are those compounds having the formula $R(R')_2N^+R^2COO^-$ wherein R is a $C_6$–$C_{18}$ hydrocarbyl group, each $R^1$ is typically $C_1$–$C_3$ alkyl, and $R^2$ is a $C_1$–$C_5$ hydrocarbyl group. Preferred betaines are $C_{12-18}$ dimethyl-ammonia hexanoate and the $C_{10-18}$ acylamidopropane (or ethane) dimethyl (or diethyl) betaines. Complex betaine surfactants are also suitable for use herein.

Water-Soluble Builder Compound

The detergent compositions of the present invention preferably contain a water-soluble builder compound, typically present at a level of from 1% to 80% by weight, preferably from 10% to 70% by weight, most preferably from 20% to 60% by weight of the composition.

Suitable water-soluble builder compounds include the water soluble monomeric polycarboxylates, or their acid forms, homo or copolymeric polycarboxylic acids or their salts in which the polycarboxylic acid comprises at least two carboxylic radicals separated from each other by not more that two carbon atoms, borates, phosphates, and mixtures of any of the foregoing.

The carboxylate or polycarboxylate builder can be monomeric or oligomeric in type although monomeric polycarboxylates are generally preferred for reasons of cost and performance.

Suitable carboxylates containing one carboxy group include the water soluble salts of lactic acid, glycolic acid and ether derivatives thereof. Polycarboxylates containing two carboxy groups include the water-soluble salts of succinic acid, malonic acid, (ethylenedioxy) diacetic acid, maleic acid, diglycolic acid, tartaric acid. tartronic acid and fumaric acid, as well as the ether carboxylates and the sulfinyl carboxylates. Polycarboxylates containing three carboxy groups include, in particular, water-soluble citrates, aconitrates and citraconates as well as succinate derivatives such as the carboxymethyloxysuccinates described in British Patent No. 1,379,241, lactoxysuccinates described in British Patent No. 1,389,732, and aminosuccinates described in Netherlands Application 7205873, and the oxypolycarboxylate materials such as 2-oxa-1,1,3-propane tricarboxylates described in British Patent No. 1,387,447.

Polycarboxylates containing four carboxy groups include oxydisuccinates disclosed in British Patent No. 1,261,829, 1,1,2,2-ethane tetracarboxylates, 1,1,3,3-propane tetracarboxylates and 1,1,2,3-propane tetracarboxylates. Polycarboxylates containing sulfo substituents include the sulfosuccinate derivatives disclosed in British Patent Nos. 1,398, 421 and 1,398,422 and in U.S. Pat. No. 3,936,448, and the sulfonated pyrolysed citrates described in British Patent No. 1,439,000. Preferred polycarboxylates are hydroxycarboxylates containing up to three carboxy groups per molecule, more particularly citrates.

Borate builders, as well as builders containing borate-forming materials that can produce borate under detergent storage or wash conditions are useful water-soluble builders herein.

Suitable examples of water-soluble phosphate builders are the alkali metal tripolyphosphates, sodium, potassium and ammonium pyrophosphate, sodium and potassium and ammonium pyrophosphate, sodium and potassium orthophosphate, sodium polymeta/phosphate in which the degree of polymerization ranges from about 6 to 21, and salts of phytic acid.

Partially Soluble or Insoluble Builder Compound

The detergent compositions of the present invention may contain a partially soluble or insoluble builder compound, typically present at a level of from 1% to 80% by weight, preferably from 10% to 70% by weight, most preferably from 20% to 60% weight of the composition.

Examples of largely water insoluble builders include the sodium aluminosilicates.

Suitable aluminosilicate zeolites have the unit cell formula $Na_z[(AlO_2)_z(SiO_2)y].xH_2O$ wherein z and y are at least 6; the molar ratio of z to y is from 1.0 to 0.5 and x is at least 5, preferably from 7.5 to 276, more preferably from 10 to 264. The aluminosilicate material are in hydrated form and are preferably crystalline, containing from 10% to 28%, more preferably from 18% to 22% water in bound form.

The aluminosilicate zeolites can be naturally occurring materials, but are preferably synthetically derived. Synthetic crystalline aluminosilicate ion exchange materials are available under the designations Zeolite A, Zeolite B, Zeolite P, Zeolite X, Zeolite HS and mixtures thereof. Zeolite A has the formula $$Na_{12}[AlO_2)_{12}(SiO_2)_{12}].xH_2O$$

wherein x is from 20 to 30, especially 27. Zeolite X has the formula $Na_{86}[(AlO_2)_{86}(SiO_2)_{106}]. 276H_2O$.

Preferred crystalline layered silicates for use herein have the general formula $$NaMSi_xO_{2x+1}.yH_2O$$

wherein M is sodium or hydrogen, x is a number from 1.9 to 4 and y is a number from 0 to 20. Crystalline layered sodium silicates of this type are disclosed in EP-A-0164514 and methods for their preparation are disclosed in DE-A-3417649 and DE-A-3742043. Herein, x in the general formula above preferably has a value of 2, 3 or 4 and is preferably 2. The most preferred material is δ-Na$_2$Si$_2$O$_5$, available from Hoechst AG as NaSKS-6.

Organic Peroxyacid Bleaching System

A preferred feature of detergent compositions of the invention is an organic peroxyacid bleaching system. In one preferred execution the bleaching system contains a hydrogen peroxide source and an organic peroxyacid bleach precursor compound. The production of the organic peroxyacid occurs by an in situ reaction of the precursor with a source of hydrogen peroxide. Preferred sources of hydrogen peroxide include inorganic perhydrate bleaches. In an alternative preferred execution a preformed organic peroxyacid is incorporated directly into the composition. Compositions containing mixtures of a hydrogen peroxide source and organic peroxyacid precursor in combination with a preformed organic peroxyacid are also envisaged.

Inorganic Perhydrate Bleaches

Inorganic perhydrate salts are a preferred source of hydrogen peroxide. These salts are normally incorporated in the form of the alkali metal, preferably sodium salt at a level of from 1% to 40% by weight, more preferably from 2% to 30% by weight and most preferably from 5% to 25% by weight of the compositions.

Examples of inorganic perhydrate salts include perborate, percarbonate, perphosphate, persulfate and persilicate salts. The inorganic perhydrate salts are normally the alkali metal salts. The inorganic perhydrate salt may be included as the crystalline solid without additional protection. For certain perhydrate salts however, the preferred executions of such granular compositions utilize a coated form of the material which provides better storage stability for the perhydrate salt in the granular product. Suitable coatings comprise inorganic salts such as alkali metal silicate, carbonate or borate salts or mixtures thereof, or organic materials such as waxes, oils, or fatty soaps.

Sodium perborate is a preferred perhydrate salt and can be in the form of the monohydrate of nominal formula NaBO$_2$H$_2$O$_2$ or the tetrahydrate NaBO$_2$H$_2$O$_2$.3H$_2$O.

Alkali metal percarbonates, particularly sodium percarbonate are preferred perhydrates herein. Sodium percarbonate is an addition compound having a formula corresponding to 2Na$_2$CO$_3$.3H$_2$O$_2$, and is available commercially as a crystalline solid.

Potassium peroxymonopersulfate is another inorganic perhydrate salt of use in the detergent compositions herein.

Peroxyacid Bleach Precursor

Peroxyacid bleach precursors are compounds which react with hydrogen peroxide in a perhydrolysis reaction to produce a peroxyacid. Generally peroxyacid bleach precursors may be represented as

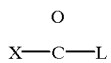

where L is a leaving group and X is essentially any functionality, such that on perhydrolysis the structure of the peroxyacid produced is

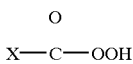

Peroxyacid bleach precursor compounds are preferably incorporated at a level of from 0.5% to 20% by weight, more preferably from 1% to 15% by weight, most preferably from 1.5% to 10% by weight of the detergent compositions.

Suitable peroxyacid bleach precursor compounds typically contain one or more N— or O—acyl groups, which precursors can be selected from a wide range of classes. Suitable classes include anhydrides, esters, imides, lactams and acylated derivatives of imidazoles and oximes. Examples of useful materials within these classes are disclosed in GB-A-1586789. Suitable esters are disclosed in GB-A-836988, 864798, 1147871, 2143231 and EP-A-0170386.

Leaving Groups

The leaving group, hereinafter L group, must be sufficiently reactive for the perhydrolysis reaction to occur within the optimum time frame (e.g., a wash cycle). However, if L is too reactive, this activator will be difficult to stabilize for use in a bleaching composition.

Preferred L groups are selected from the group consisting of:

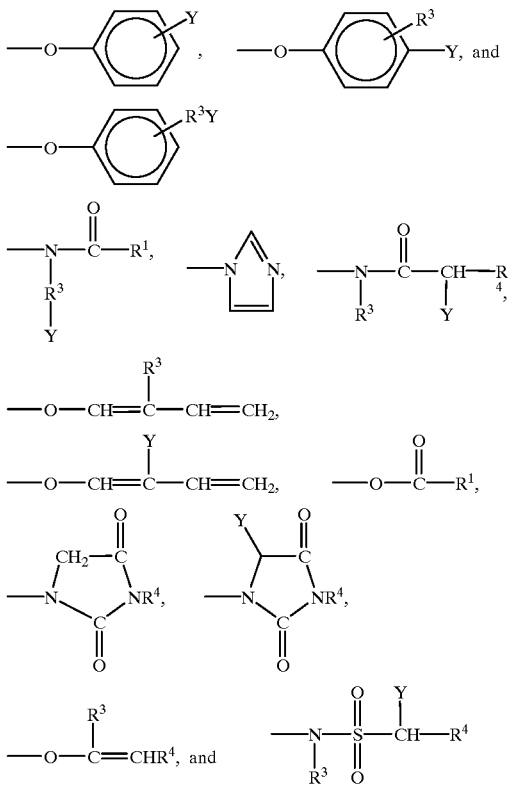

and mixtures thereof, wherein $R^1$ is an alkyl, aryl, or alkaryl group containing from 1 to 14 carbon atoms, $R^3$ is an alkyl chain containing from 1 to 8 carbon atoms, $R^4$ is H or $R^3$, and Y is H or a solubilizing group. Any of $R^1$, $R^3$ and $R^4$ may be substituted by essentially any functional group including, for example alkyl, hydroxy, alkoxy, halogen, amine, nitrosyl, amide and ammonium or alkyl ammonium groups.

The preferred solubilizing groups are —SO$_3^-$M$^+$, —CO$_2^-$M$^+$, —SO$_4^-$M$^+$, —N$^+$(R$^3$)$_4$X$^-$ and O<—N(R$^3$)$_3$ and most preferably —SO$_3^-$M$^+$ and —CO$_2^-$M$^+$ wherein $R^3$ is an alkyl chain containing from 1 to 4 carbon atoms, M is a cation which provides solubility to the bleach activator and X is an anion which provides solubility to the bleach activator. Preferably, M is an alkali metal, ammonium or substituted ammonium cation, with sodium and potassium being most preferred, and X is a halide, hydroxide, methylsulfate or acetate anion.

Alkyl Percarboxylic Acid Bleach Precursors

Alkyl percarboxylic acid bleach precursors form percarboxylic acids on perhydrolysis. Preferred precursors of this type provide peracetic acid on perhydrolysis.

Preferred alkyl percarboxylic precursor compounds of the imide type include the N—,N,N¹N¹ tetra acetylated alkylene diamines wherein the alkylene group contains from 1 to 6 carbon atoms, particularly those compounds in which the alkylene group contains 1, 2 and 6 carbon atoms. Tetraacetyl ethylene diamine (TAED) is particularly preferred.

Other preferred alkyl percarboxylic acid precursors include sodium 3,5,5-tri-methyl hexanoyloxybenzene sulfonate (iso-NOBS), sodium nonanoyloxybenzene sulfonate (NOBS), sodium acetoxybenzene sulfonate (ABS) and pentaacetyl glucose.

Amide Substituted Alkyl Peroxyacid Precursors

Amide substituted alkyl peroxyacid precursor compounds are suitable herein, including those of the following general formulae:

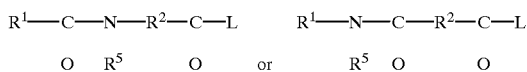

wherein $R^1$ is an alkyl group with from 1 to 14 carbon atoms, $R^2$ is an alkylene group containing from 1 to 14 carbon atoms, and $R^5$ is H or an alkyl group containing 1 to 10 carbon atoms and L can be essentially any leaving group. Amide substituted bleach activator compounds of this type are described in EP-A-0170386.

Perbenzoic Acid Precursor

Perbenzoic acid precursor compounds provide perbenzoic acid on perhydrolysis. Suitable O-acylated perbenzoic acid precursor compounds include the substituted and unsubstituted benzoyl oxybenzene sulfonates, and the benzoylation products of sorbitol, glucose, and all saccharides with benzoylating agents, and those of the imide type including N-benzoyl succinimide, tetrabenzoyl ethylene diamine and the N-benzoyl substituted ureas. Suitable imidazole type perbenzoic acid precursors include N-benzoyl imidazole and N-benzoyl benzimidazole. Other useful N-acyl group-containing perbenzoic acid precursors include N-benzoyl pyrrolidone, dibenzoyl taurine and benzoyl pyroglutamic acid.

Cationic Peroxyacid Precursors

Cationic peroxyacid precursor compounds produce cationic peroxyacids on perhydrolysis.

Typically, cationic peroxyacid precursors are formed by substituting the peroxyacid part of a suitable peroxyacid precursor compound with a positively charged functional group, such as an ammonium or alkyl ammonium group, preferably an ethyl or methyl ammonium group. Cationic peroxyacid precursors are typically present in the solid detergent compositions as a salt with a suitable anion, such as a halide ion.

The peroxyacid precursor compound to be so cationically substituted may be a perbenzoic acid, or substituted derivative thereof, precursor compound as described hereinbefore. Alternatively, the peroxyacid precursor compound may be an alkyl percarboxylic acid precursor compound or an amide substituted alkyl peroxyacid precursor as described hereinafter.

Cationic peroxyacid precursors are described in U.S. Pat. Nos. 4,904,406; 4,751,015; 4,988,451; 4,397,757; 5,269,962; 5,127,852; 5,093,022; 5,106,528; U.K. 1,382,594; EP 475,512, 458,396 and 284,292; and in JP 87-318,332.

Examples of preferred cationic peroxyacid precursors are described in UK Patent Application No. 9407944.9 and U.S. patent application Ser. Nos. 08/298903, 08/298650, 08/298904 and 08/298906.

Suitable cationic peroxyacid precursors include any of the ammonium or alkyl ammonium substituted alkyl or benzoyl oxybenzene sulfonates, N-acylated caprolactams, and monobenzoyltetracetyl glucose benzoyl peroxides. Preferred cationic peroxyacid precursors of the N-acylated caprolactam class include the trialkyl ammonium methylene benzoyl caprolactams and the trialkyl ammonium methylene alkyl caprolactams.

Benzoxazin Organic Peroxyacid Precursors

Also suitable are precursor compounds of the benzoxazin-type, as disclosed for example in EP-A-332,294 and EP-A482,807, particularly those having the formula:

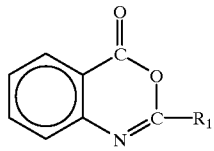

wherein $R_1$ is H, alkyl, alkaryl, aryl, or arylalkyl.

Preformed Organic Peroxyacid

The organic peroxyacid bleaching system may contain, in addition to, or as an alternative to, an organic peroxyacid bleach precursor compound, a preformed organic peroxyacid, typically at a level of from 1% to 15% by weight, more preferably from 1% to 10% by weight of the composition.

A preferred class of organic peroxyacid compounds are the amide substituted compounds of the following general formulae:

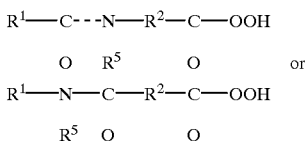

wherein $R^1$ is an alkyl, aryl or alkaryl group with from 1 to 14 carbon atoms, $R^2$ is an alkylene, arylene, and alkarylene group containing from 1 to 14 carbon atoms, and $R^5$ is H or an alkyl, aryl, or alkaryl group containing 1 to 10 carbon atoms. Amide substituted organic peroxyacid compounds of this type are described in EP-A-0170386.

Other organic peroxyacids include diacyl and tetraacylperoxides, especially diperoxydodecanedioc acid, diperoxytetradecanedioc acid and diperoxyhexadecanedioc acid. Mono- and diperazelaic acid, mono- and diperbrassylic acid and N-phthaloylaminoperoxicaproic acid are also suitable herein.

Bleach Catalyst

The compositions optionally contain a transition metal containing bleach catalyst. One suitable type of bleach catalyst is a catalyst system comprising a heavy metal cation of defined bleach catalytic activity, such as copper, iron or manganese cations, an auxiliary metal cation having little or no bleach catalytic activity, such as zinc or aluminum cations, and a sequestrant having defined stability constants for the catalytic and auxiliary metal cations, particularly ethylenediaminetetraacetic acid, ethylenediaminetetra (methylenephosphonic acid) and water-soluble salts thereof. Such catalysts are disclosed in U.S. Pat. No. 4,430,243.

Other types of bleach catalysts include the manganese-based complexes disclosed in U.S. Pat. Nos. 5,246,621 and 5,244,594. Preferred examples of these catalysts include $Mn^{IV}_2(u-O)_3(1,4,7$-trimethyl-1,4,7-triazacyclononane$)_2$-$(PF_6)_2$, $Mn^{III}_2(u-O)_1(u-OAc)_2(1,4,7$-trimethyl-1,4,7-triazacyclononane$)_2$-$(ClO_4)_2$, $Mn^{IV}_4(u-O)_6(1,4,7$- triazacyclononane)$_4$-(ClO$_4$)$_2$, Mn$^{III}$Mn$^{IV}_4$(u-O)$_1$(u-OAc)$_2$-(1,4,7-trimethyl-1,4,7-triazacyclononane)$_2$-(ClO$_4$)$_3$, and mixtures thereof. Others are described in European patent application publication no. 549,272. Other ligands suitable for use herein include 1,5,9-timethyl-1,5,9-triazacyclododecane, 2-methyl-1,4,7-triazacyclononane, 2-methyl-1,4,7-triazacyclononan 1,2,4,7-tetramethyl-1,4,7-triazacyclononane, and mixtures thereof.

For examples of suitable bleach catalysts see U.S. Pat. Nos. 4,246,612 and 5,227,084. See also U.S. Pat. No. 5,194,416 which teaches mononuclear manganese (IV) complexes such as Mn(1,4,7-trimethyl-1,4,7-triazacyclononane)(OCH$_3$)$_3$-(PF$_6$). Still another type of bleach catalyst, as disclosed in U.S. Pat. No. 5,114,606, is a water-soluble complex of manganese (III), and/or (IV) with a ligand which is a non-carboxylate polyhydroxy compound having at least three consecutive C—OH groups. Other examples include binuclear Mn complexed with tetra-N-dentate and bi-N-dentate ligands, including N$_4$Mn$^{III}$(u-O)$_2$Mn$^{IV}$N$_4$)$^+$ and [Bipy$_2$Mn$^{III}$(u-O)$_2$Mn$^{IV}$bipy$_2$]-(ClO$_4$)$_3$.

Further suitable bleach catalysts are described, for example, in European patent application No. 408,131 (cobalt complex catalysts), European patent applications, publication nos. 384,503, and 306,089 (metallo-porphyrin catalysts), U.S. Pat. No. 4,728,455 (manganese/multidentate ligand catalyst), U.S. Pat. No. 4,711,748 and European patent application, publication no. 224,952, (absorbed manganese on aluminosilicate catalyst), U.S. Pat. No. 4,601,845 (aluminosilicate support with manganese and zinc or magnesium salt), U.S. Pat. No. 4,626,373 (manganese/ligand catalyst), U.S. Pat. No. 4,119,557 (ferric complex catalyst), German Pat. specification 2,054,019 (cobalt chelant catalyst) Canadian 866,191 (transition metal-containing salts), U.S. Pat. No. 4,430,243 (chelants with manganese cations and non-catalytic metal cations), and U.S. Pat. No. 4,728,455 (manganese gluconate catalysts).

Heavy Metal Ion Sequestrant

The detergent compositions of the invention preferably contain as an optional component a heavy metal ion sequestrant. By heavy metal ion sequestrant it is meant herein components which act to sequester (chelate) heavy metal ions. These components may also have calcium and magnesium chelation capacity, but preferentially they show selectivity to binding heavy metal ions such as iron, manganese and copper.

Heavy metal ion sequestrants are generally present at a level of from 0.005% to 20%, preferably from 0.1% to 10%, more preferably from 0.25% to 7.5% and most preferably from 0.5% to 5% by weight of the compositions.

Suitable heavy metal ion sequestrants for use herein include organic phosphonates, such as the amino alkylene poly (alkylene phosphonates), alkali metal ethane 1-hydroxy disphosphonates and nitrilo trimethylene phosphonates.

Preferred among the above species are diethylene triamine penta (methylene phosphonate), ethylene diamine tri (methylene phosphonate) hexamethylene diamine tetra (methylene phosphonate) and hydroxy-ethylene 1,1 diphosphonate.

Other suitable heavy metal ion sequestrant for use herein include nitrilotriacetic acid and polyaminocarboxylic acids such as ethylenediaminotetracetic acid, ethylenetriamine pentacetic acid, ethylenediamine disuccinic acid, ethylenediamine diglutaric acid, 2-hydroxypropylenediamine disuccinic acid or any salts thereof. Especially preferred is ethylenediamine-N,N-disuccinic acid (EDDS) or the alkali metal, alkaline earth metal, ammonium, or substituted ammonium salts thereof, or mixtures thereof.

Other suitable heavy metal ion sequestrants for use herein are iminodiacetic acid derivatives such as 2-hydroxyethyl diacetic acid or glyceryl imino diacetic acid, described in EP-A-317,542 and EP-A-399,133. The iminodiacetic acid-N-2-hydroxypropyl sulfonic acid and aspartic acid N-carboxymethyl N-2-hydroxypropyl-3-sulfonic acid sequestrants described in EP-A-516,102 are also suitable herein. The β-alanine-N,N'-diacetic acid, aspartic acid-N,N'-diacetic acid, aspartic acid-N-monoacetic acid and imino-disuccinic acid sequestrants described in EP-A-509,382 are also suitable.

EP-A-476,257 describes suitable amino based sequestrants. EP-A-510,331 describes suitable sequestrants derived from collagen, keratin or casein. EP-A-528,859 describes a suitable alkyl iminodiacetic acid sequestrant. Dipicolinic acid and 2-phosphonobutane-1,2,4-tricarboxylic acid are also suitable. Glycinamide-N,N'-disuccinic acid (GADS), ethylenediamine-N-N'-diglutaric acid (EDDG) and 2-hydroxypropylenediamine-N-N'-disuccinic acid (HPDDS) are also suitable.

Enzyme

Another preferred ingredient useful in the detergent compositions is one or more additional enzymes.

Preferred additional enzymatic materials include the commercially available lipases, cutinases, amylases, neutral and alkaline proteases, esterases, cellulases, pectinases, lactases and peroxidases conventionally incorporated into detergent compositions. Suitable enzymes are discussed in U.S. Pat. Nos. 3,519,570 and 3,533,139.

Preferred commercially available protease enzymes include those sold under the tradenames Alcalase, Savinase, Primase, Durazym, and Esperase by Novo Industries A/S (Denmark), those sold under the tradename Maxatase, Maxacal and Maxapem by Gist-Brocades, those sold by Genencor International, and those sold under the tradename Opticlean and Optimase by Solvay Enzymes. Protease enzyme may be incorporated into the compositions in accordance with the invention at a level of from 0.0001% to 4% active enzyme by weight of the composition.

Preferred amylases include, for example, α-amylases obtained from a special strain of B licheniformis, described in more detail in GB-1,269,839 (Novo). Preferred commercially available amylases include for example, those sold under the tradename Rapidase by Gist-Brocades, and those sold under the tradename Termamyl and BAN by Novo Industries A/S. Amylase enzyme may be incorporated into the composition in accordance with the invention at a level of from 0.0001% to 2% active enzyme by weight of the composition.

Lipolytic enzyme may be present at levels of active lipolytic enzyme of from 0.0001% to 2% by weight, preferably 0.001% to 1% by weight, most preferably from 0.001% to 0.5% by weight of the compositions.

The lipase may be fungal or bacterial in origin being obtained, for example, from a lipase producing strain of Humicola sp., Thermomyces sp. or Pseudomonas sp. including *Pseudomonas pseudoalcaligenes* or *Pseudomas fluorescens*. Lipase from chemically or genetically modified mutants of these strains are also useful herein. A preferred lipase is derived from *Pseudomonas pseudoalcaligenes*, which is described in Granted European Patent, EP-B-0218272.

Another preferred lipase herein is obtained by cloning the gene from *Humicola lanuginosa* and expressing the gene in *Aspergillus oryza*, as host, as described in European Patent Application, EP-A-0258 068, which is commercially available from Novo Industri A/S, Bagsvaerd, Denmark, under the trade name Lipolase. This lipase is also described in U.S. Pat. No. 4,810,414, Huge-Jensen et al, issued Mar. 7, 1989.

Organic Polymeric Compound

Organic polymeric compounds are preferred additional components of the detergent compositions in accord with the invention, and are preferably present as components of any particulate components where they may act such as to bind the particulate component together. By organic polymeric compound it is meant herein essentially any polymeric organic compound commonly used as dispersants, and anti-redeposition and soil suspension agents in detergent compositions, including any of the high molecular weight organic polymeric compounds described as clay flocculating agents herein.

Organic polymeric compound is typically incorporated in the detergent compositions of the invention at a level of from 0.1% to 30%, preferably from 0.5% to 15%, most preferably from 1% to 10% by weight of the compositions.

Examples of organic polymeric compounds include the water soluble organic homo- or co-polymeric polycarboxylic acids or their salts in which the polycarboxylic acid comprises at least two carboxyl radicals separated from each other by not more than two carbon atoms. Polymers of the latter type are disclosed in GB-A-1,596,756. Examples of such salts are polyacryiates of MWt 2000–5000 and their copolymers with maleic anhydride, such copolymers having a molecular weight of from 20,000 to 100,000, especially 40,000 to 80,000.

The polyamino compounds are useful herein including those derived from aspanic acid such as those disclosed in EP-A-305282, EP-A-305283 and EP-A-351629.

Terpolymers containing monomer units selected from maleic acid, acrylic acid, polyaspartic acid and vinyl alcohol, particularly those having an average molecular weight of from 5,000 to 10,000, are also suitable herein.

Other organic polymeric compounds suitable for incorporation in the detergent compositions herein include cellulose derivatives such as methylcellulose, carboxymethylcellulose, hydroxypropylmethylcellulose and hydroxyethylcellulose.

Further useful organic polymeric compounds are the polyethylene glycols, particularly those of molecular weight 1000–10000, more particularly 2000 to 8000 and most preferably about 4000.

Another organic compound, which is a preferred clay dispersant/anti-redeposition agent, for use herein, can be the ethoxylated cationic monoamines and diamines of the formula:

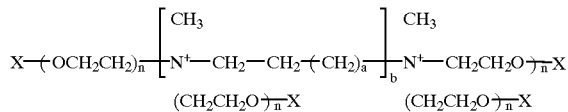

wherein X is a noniomc group selected from the group consisting of H, $C_1$–$C_4$ alkyl or hydroxyalkyl ester or ether groups, and mixtures thereof, a is from 0 to 20, preferably from 0 to 4 (e.g. ethylene, propylene, hexamethylene) b is 1 or 0; for cationic monoamines (b=0), n is at least 16, with a typical range of from 20 to 35; for cationic diamines (b=1), n is at least about 12 with a typical range of from about 12 to about 42.

Other dispersants/anti-redeposition agents for use herein are described in EP-B-011965 and U.S. Pat. Nos. 4,659,802 and 4,664,848.

Suds Suppressing System

The detergent compositions of the invention, when formulated for use in machine washing compositions, preferably comprise a suds suppressing system present at a level of from 0.01% to 15%, preferably from 0.05% to 10%, most preferably from 0.1% to 5% by weight of the composition.

Suitable suds suppressing systems for use herein may comprise essentially any known antifoam compound, including, for example silicone antifoam compounds and 2-alkyl alcanol antifoam compounds.

By antifoam compound it is meant herein any compound or mixtures of compounds which act such as to depress the foaming or sudsing produced by a solution of a detergent composition, particularly in the presence of agitation of that solution.

Particularly preferred antifoam compounds for use herein are silicone antifoam compounds defined herein as any antifoam compound including a silicone component. Such silicone antifoam compounds also typically contain a silica component. The term "silicone" as used herein, and in general throughout the industry, encompasses a variety of relatively high molecular weight polymers containing siloxane units and hydrocarbyl group of various types. Preferred silicone antifoam compounds are the siloxanes, particularly the polydimethylsiloxanes having trimethylsilyl end blocking units.

Other suitable antifoam compounds include the monocarboxylic fatty acids and soluble salts thereof. These materials are described in U.S. Pat. No. 2,954,347, issued Sep. 27, 1960 to Wayne St. John. The monocarboxylic fatty acids, and salts thereof, for use as suds suppressor typically have hydrocarbyl chains of 10 to 24 carbon atoms, preferably 12 to 18 carbon atoms. Suitable salts include the alkali metal salts such as sodium, potassium, and lithium salts, and ammonium and alkanolammonium salts.

Other suitable antifoam compounds include, for example, high molecular weight fatty esters (e.g. fatty acid triglycerides), fatty acid esters of monovalent alcohols, aliphatic $C_{18}$–$C_{40}$ ketones (e.g. stearone) N-alkylated amino triazines such as tri- to hexa-alkylmelamines or di- to tetra alkyldiamine chlortriazines formed as products of cyanuric chloride with two or three moles of a primary or secondary amine containing 1 to 24 carbon atoms, propylene oxide, bis stearic acid amide and monostearyl di-alkali metal (e.g. sodium, potassium, lithium) phosphates and phosphate esters.

A preferred suds suppressing system comprises
(a) antifoam compound, preferably silicone antifoam compound, most preferably a silicone antifoam compound comprising in combination
(i) polydimethyl siloxane, at a level of from 50% to 99%, preferably 75% to 95% by weight of the silicone antifoam compound; and
(ii) silica, at a level of from 1% to 50%, preferably 5% to 25% by weight of the silicone/silica antifoam compound;
wherein said silica/silicone antifoam compound is incorporated at a level of from 5% to 50%, preferably 10% to 40% by weight;
(b) a dispersant compound, most preferably comprising a silicone glycol rake copolymer with a polyoxyalkylene content of 72–78% and an ethylene oxide to propylene oxide ratio of from 1:0.9 to 1:1.1, at a level of from 0.5% to 10%, preferably 1% to 10% by weight; a particularly preferred silicone glycol rake copolymer of this type is DCO544, commercially available from DOW Corning under the tradename DCO0544;

(c) an inert carrier fluid compound, most preferably comprising a $C_{16}$–$C_{18}$ ethoxylated alcohol with a degree of ethoxylation of from 5 to 50, preferably 8 to 15, at a level of from 5% to 80%, preferably 10% to 70%, by weight;

A highly preferred particulate suds suppressing system is described in EP-A-0210731 and comprises a silicone antifoam compound and an organic carrier material having a melting point in the range 50° C. to 85° C., wherein the organic carrier material comprises a monoester of glycerol and a fatty acid having a carbon chain containing from 12 to 20 carbon atoms. EP-A-0210721 discloses other preferred particulate suds suppressing systems wherein the organic carrier material is a fatty acid or alcohol having a carbon chain containing from 12 to 20 carbon atoms, or a mixture thereof, with a melting point of from 45° C. to 80° C.

Clay Softening System

The detergent compositions may contain a clay softening system comprising a clay mineral compound and optionally a clay flocculating agent.

The clay mineral compound is preferably a smectite clay compound. Smectite clays are disclosed in the U.S. Pat. Nos. 3,862,058, 3,948,790, 3,954,632 and 4,062,647. European Patents Nos. EP-A-299,575 and EP-A-313,146 in the name of the Procter and Gamble Company describe suitable organic polymeric clay flocculating agents.

Polymeric Dye Transfer Inhibiting Agents

The detergent compositions herein may also comprise from 0.01% to 10%, preferably from 0.05% to 0.5% by weight of polymeric dye transfer inhibiting agents.

The polymeric dye transfer inhibiting agents are preferably selected from polyamine N-oxide polymers, copolymers of N-vinylpyrrolidone and N-vinylimidazole, polyvinylpyrrolidonepolymers or combinations thereof.

a) Polyamine N-oxide Polymers

Polyamine N-oxide polymers suitable for use herein contain units having the following structure formula:

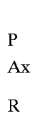

(I)

wherein

P is a polymerisable unit, and

A is —O—, —S—, —N—; x is 0 or 1;

R are aliphatic, ethoxylated aliphatic, aromatic, heterocyclic or alicyclic groups or any combination thereof whereto the nitrogen of the N—O group can be attached or wherein the nitrogen of the N—O group is part of these groups.

The N—O group can be represented by the following general structures:

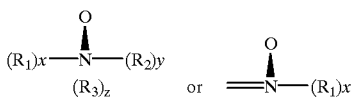

wherein R1, R2, and R3 are aliphatic groups, aromatic, heterocyclic or alicyclic groups or combinations thereof, x or/and y or/and z is 0 or 1 and wherein the nitrogen of the N—O group can be attached or wherein the nitrogen of the N—O group forms part of these groups. The N—O group can be part of the polymerisable unit (P) or can be attached to the polymeric backbone or a combination of both.

Suitable polyamine N-oxides wherein the N—O group forms part of the polymerisable unit comprise polyamine N-oxides wherein R is selected from aliphatic, aromatic, alicyclic or heterocyclic groups. One class of said polyamine N-oxides comprises the group of polyamine N-oxides wherein the nitrogen of the N—O group forms part of the R-group. Preferred polyamine N-oxides are those wherein R is a heterocyclic group such as pyrridine, pyrrole, imidazole, pyrrolidine, piperidine, quinoline, acridine and derivatives thereof.

Other suitable polyamine N-oxides are the polyamine oxides whereto the N—O group is attached to the polymerisable unit. A preferred class of these polyamine N-oxides comprises the polyamine N-oxides having the general formula (I) wherein R is an aromatic, heterocyclic or alicyclic groups wherein the nitrogen of the N—O functional group is part of said R group. Examples of these classes are polyamine oxides wherein R is a heterocyclic compound such as pyrridine, pyrrole, imidazole and derivatives thereof.

The polyamine N-oxides can be obtained in almost any degree of polymerisation. The degree of polymerisation is not critical provided the material has the desired water-solubility and dye-suspending power. Typically, the average molecular weight is within the range of 500 to 1000,000.

b) Copolymers of N-vinylpyrrolidone and N-vinylimidazole

Suitable herein are copolymers of N-vinylimidazole and N-vinylpyrrolidone having an average molecular weight range of from 5,000 to 50,000. The preferred copolymers have a molar ratio of N-vinylimidazole to N-vinylpyrrolidone from 1 to 0.2.

c) Polyvinylpyrrolidone

The detergent compositions herein may also utilize polyvinylpyrrolidone ("PVP") having an average molecular weight of from 2,500 to 400,000. Suitable polyvinylpyrrolidones are commercially available from ISP Corporation, New York, N.Y. and Montreal, Canada under the product names PVP K-15 (viscosity molecular weight of 10,000), PVP K-30 (average molecular weight of 40,000), PVP K-60 (average molecular weight of 160,000), and PVP K-90 (average molecular weight of 360,000). PVP K-15 is also available from ISP Corporation. Other suitable polyvinylpyrrolidones which are commercially available from BASF Cooperation include Sokalan HP 165 and Sokalan HP 12.

d) Polyvinyloxazolidone

The detergent compositions herein may also utilize polyvinyloxazolidones as polymeric dye transfer inhibiting agents. Said polyvinyloxazolidones have an average molecular weight of from 2,500 to 400,000.

e) Polyvinylimidazole

The detergent compositions herein may also utilize polyvinylimidazole as polymeric dye transfer inhibiting agent. Said polyvinylimidazoles preferably have an average molecular weight of from 2,500 to 400,000.

Optical Brightener

The detergent compositions herein also optionally contain from about 0.005% to 5% by weight of certain types of hydrophilic optical brighteners.

Hydrophilic optical brighteners useful herein include those having the structural formula:

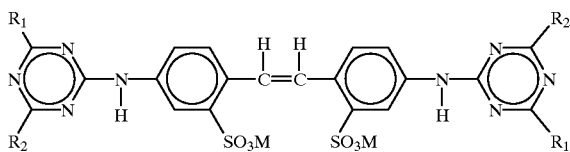

wherein $R_1$ is selected from anilino, N-2-bis-hydroxyethyl and NH-2-hydroxyethyl; $R_2$ is selected from N-2-bis-hydroxyethyl, N-2-hydroxyethyl-N-methylamino, morphilino, chloro and amino; and M is a salt-forming cation such as sodium or potassium.

When in the above formula, $R_1$ is anilino, $R_2$ is N-2-bis-hydroxyethyl and M is a cation such as sodium, the brightener is 4,4',-bis[(4-anilino-6-(N-2-bis-hydroxyethyl)-s-triazine-2-yl)amino]-2,2'-stilbenedisulfonic acid and disodium salt. This particular brightener species is commercially marketed under the tradename Tinopal-UNPA-GX by Ciba-Geigy Corporation. Tinopal-UNPA-GX is the preferred hydrophilic optical brightener useful in the detergent compositions herein.

When in the above formula, $R_1$ is anilino, $R_2$ is N-2-hydroxyethyl-N-2-methylamino and M is a cation such as sodium, the brightener is 4,4'-bis[(4-anilino-6-(N-2-hydroxyethyl-N-methylamino)-s-triazine-2-yl)amino]2,2'-stilbenedisulfonic acid disodium salt. This particular brightener species is commercially marketed under the tradename Tinopal 5BM-GX by Ciba-Geigy Corporation.

When in the above formula, $R_1$ is anilino, $R_2$ is morphilino and M is a cation such as sodium, the brightener is 4,4'-bis[(4-anilino-6-morphilino-s-triazine-2-yl)amino]2,2'-stilbenedisulfonic acid, sodium salt. This particular brightener species is commercially marketed under the tradename Tinopal AMS-GX by Ciba Geigy Corporation.

Cationic Fabric Softening Agents

Cationic fabric softening agents can also be incorporated into compositions in accordance with the present invention. Suitable cationic fabric softening agents include the water insoluble tertiary amines or dilong chain amide materials as disclosed in GB-A-1 514 276 and EP-B-0 011 340.

Cationic fabric softening agents are typically incorporated at total levels of from 0.5% to 15% by weight, normally from 1% to 5% by weight.

Other Optional Ingredients

Other optional ingredients suitable for inclusion in the compositions of the invention include perfumes, colours and filler salts, with sodium sulfate being a preferred filler salt.

pH of the Compositions

The present compositions preferably have a pH measured as a 1% solution in distilled water of at least 10.0, preferably from 10.0 to 12.5, most preferably from 10.5 to 12.0.

Form of the Compositions

The detergent composition of the invention can be made via a variety of methods, including dry-mixing and agglomerating of the various compounds comprised in the detergent composition. The acid source of the invention is preferably dry-added.

The compositions in accordance with the invention can take a variety of physical forms including granular, tablet, bar and liquid forms. The compositions are particularly the so-called concentrated granular detergent compositions adapted to be added to a washing machine by means of a dispensing device placed in the machine drum with the soiled fabric load.

The mean particle size of the base composition of granular compositions in accordance with the invention can be from 0.1 mm to 5.0 mm, but it should preferably be such that no more that 5% of particles are greater than 1.7 mm in diameter and not more than 5% of particles are less than 0.15 mm in diameter.

The term mean particle size as defined herein is calculated by sieving a sample of the composition into a number of fractions (typically 5 fractions) on a series of Tyler sieves. The weight fractions thereby obtained are plotted against the aperture size of the sieves. The mean particle size is taken to be the aperture size through which 50% by weight of the sample would pass.

The bulk density of granular detergent compositions in accordance with the present invention typically have a bulk density of at least 600 g/liter, more preferably from 650 g/liter to 1200 g/liter. Bulk density is measured by means of a simple funnel and cup device consisting of a conical funnel moulded rigidly on a base and provided with a flap valve at its lower extremity to allow the contents of the funnel to be emptied into an axially aligned cylindrical cup disposed below the funnel. The funnel is 130 mm high and has internal diameters of 130 mm and 40 mm at its respective upper and lower extremities. It is mounted so that the lower extremity is 140 mm above the upper surface of the base. The cup has an overall height of 90 mm, an internal height of 87 mm and an internal diameter of 84 mm. Its nominal volume is 500 ml.

To carry out a measurement, the funnel is filled with powder by hand pouring, the flap valve is opened and powder allowed to overfill the cup. The filled cup is removed from the frame and excess powder removed from the cup by passing a straight edged implement eg; a knife, across its upper edge. The filled cup is then weighed and the value obtained for the weight of powder doubled to provide a bulk density in g/liter. Replicate measurements are made as required.

Surfactant Agglomerate Particles

The surfactant system herein is preferably present in granular compositions in the form of surfactant agglomerate particles, which may take the form of flakes, prills, marurnes, noodles, ribbons, but preferably take the form of granules. The most preferred way to process the particles is by agglomerating powders (e.g. aluminosilicate, carbonate) with high active surfactant pastes and to control the particle size of the resultant agglomerates within specified limits. Such a process involves mixing an effective amount of powder with a high active surfactant paste in one or more agglomerators such as a pan agglomerator, a Z-blade mixer or more preferably an in-line mixer such as those manufactured by Schugi (Holland) BV, 29 Chroomstraat 8211 AS, Lelystad, Netherlands. and Gebruder Lodige Maschinenbau GmbH, D4790 Paderbom 1, Elsenerstrasse 7-9, Postfach 2050, Germany. Most preferably a high shear mixer is used, such as a Lodige CB (Trade Name).

A high active surfactant paste comprising from 50% by weight to 95% by weight, preferably 70% by weight to 85% by weight of surfactant is typically used. The paste may be pumped into the agglomerator at a temperature high enough to maintain a pumpable viscosity, but low enough to avoid degradation of the anionic surfactants used. An operating temperature of the paste of 50° C. to 80° C. is typical.

In an especially preferred embodiment of the present invention, the detergent composition has a density of greater than about 600 g/l and is in the form of powder or a granulate containing more than about 5% by weight of the alkali, preferably (bi-) carbonate or percarbonate. The carbonate material is either dry-added or delivered via agglomerates. The addition of the acid, preferably citric acid, (up to 10%)

may be introduced into the product as a dry-add, or via a separate particle.

Laundry Washing Method

Machine laundry methods herein typically comprise treating soiled laundry with an aqueous wash solution in a washing machine having dissolved or dispensed therein an effective amount of a machine laundry detergent composition in accord with the invention. By an effective amount of the detergent composition it is meant from 40 g to 300 g of product dissolved or dispersed in a wash solution of volume from 5 to 65 liters, as are typical product dosages and wash solution volumes commonly employed in conventional machine laundry methods.

In a preferred use aspect a dispensing device is employed in the washing method. The dispensing device is charged with the detergent product, and is used to introduce the product directly into the drum of the washing machine before the commencement of the wash cycle. Its volume capacity should be such as to be able to contain sufficient detergent product as would normally be used in the washing method.

Once the washing machine has been loaded with laundry the dispensing device containing the detergent product is placed inside the drum. At the commencement of the wash cycle of the washing machine water is introduced into the drum and the drum periodically rotates. The design of the dispensing device should be such that it permits containment of the dry detergent product but then allows release of this product during the wash cycle in response to its agitation as the drum rotates and also as a result of its contact with the wash water.

To allow for release of the detergent product during the wash the device may possess a number of openings through which the product may pass. Alternatively, the device may be made of a material which is permeable to liquid but impermeable to the solid product, which will allow release of dissolved product. Preferably, the detergent product will be rapidly released at the start of the wash cycle thereby providing transient localised high concentrations of product in the drum of the washing machine at this stage of the wash cycle.

Preferred dispensing devices are reusable and are designed in such a way that container integrity is maintained in both the dry state and during the wash cycle. Especially preferred dispensing devices for use with the composition of the invention have been described in the following patents; GB-B-2, 157, 717, GB-B-2, 157, 718, EP-A-0201376, EP-A-0288345 and EP-A-0288346. An article by J. Bland published in *Manufacturing Chemist,* November 1989, pages 41–46 also describes especially preferred dispensing devices for use with granular laundry products which are of a type commonly know as the "granulette". Another preferred dispensing device for use with the compositions of this invention is disclosed in PCT Patent Application No. WO94/11562.

Especially preferred dispensing devices are disclosed in European Patent Application Publication Nos. 0343069 & 0343070. The latter Application discloses a device comprising a flexible sheath in the form of a bag extending from a support ring defining an orifice, the orifice being adapted to admit to the bag sufficient product for one washing cycle in a washing process. A portion of the washing medium flows through the orifice into the bag, dissolves the product, and the solution then passes outwardly through the orifice into the washing medium. The support ring is provided with a masking arrangement to prevent egress of wetted, undissolved, product, this arrangement typically comprising radially extending walls extending from a central boss in a spoked wheel configuration, or a similar structure in which the walls have a helical form.

Alternatively, the dispensing device may be a flexible container, such as a bag or pouch. The bag may be of fibrous construction coated with a water impermeable protective material so as to retain the contents, such as is disclosed in European published Patent Application No. 0018678. Alternatively it may be formed of a water-insoluble synthetic polymeric material provided with an edge seal or closure designed to rupture in aqueous media as disclosed in European published Patent Application Nos. 0011500, 0011501, 0011502, and 0011968. A convenient form of water frangible closure comprises a water soluble adhesive disposed along and sealing one edge of a pouch formed of a water impermeable polymeric film such as polyethylene or polypropylene.

Packaging for the Compositions

Commercially marketed executions of the bleaching compositions can be packaged in any suitable container including those constructed from paper, cardboard, plastic materials and any suitable laminates. A preferred packaging execution is described in European Application No. 94921505.7.

Abbreviations used in Following Examples

In the detergent compositions, the abbreviated component identifications have the following meanings:

| | |
|---|---|
| LAS: | Sodium linear $C_{12}$ alkyl benzene sulfonate |
| TAS: | Sodium tallow alkyl sulfate |
| C45AS: | Sodium $C_{14}$–$C_{15}$ linear alkyl sulfate |
| CxyEzS: | Sodium $C_{1x}$–$C_{1y}$ branched alkyl sulfate condensed with z moles of ethylene oxide |
| C45E7: | A $C_{14-15}$ predominantly linear primary alcohol condensed with an average of 7 moles of ethylene oxide |
| C25E3: | A $C_{12-15}$ branched primary alcohol condensed with an average of 3 moles of ethylene oxide |
| C25E5: | A $C_{12-15}$ branched primary alcohol condensed with an average of 5 moles of ethylene oxide |
| CEQ: | $R_1COOCH_2CH_2.N^+(CH_3)_3$ with $R_1 = C_{11}$–$C_{13}$ |
| QAS I: | $R_2.N^+(CH_3)_2(C_2H_4OH)$ with $R_2 = C_{12}$–$C_{14}$ |
| QAS II: | $R_2.N^+(CH_3)(C_2H_4OH)_2$ with $R_2 = C_{10}$–$C_{14}$ |
| Soap: | Sodium linear alkyl carboxylate derived from an 80/20 mixture of tallow and coconut oils. |
| TFAA: | $C_{16}$–$C_{18}$ alkyl N-methyl glucamide |
| TPKFA: | C12–C14 topped whole cut fatty acids |
| STPP: | Anhydrous sodium tripolyphosphate |
| Zeolite A: | Hydrated Sodium Aluminosilicate of formula $Na_{12}(AlO_2SiO_2)_{12}.27H_2O$ having a primary particle size in the range from 0.1 to 10 micrometers |
| NaSKS-6: | Crystalline layered silicate of formula $\delta$-$Na_2Si_2O_5$ |
| Citric acid: | Anhydrous citric acid |
| Carbonate: | Anhydrous sodium carbonate with a particle size between 200 $\mu$m and 900 $\mu$m |
| Bicarbonate: | Anhydrous sodium bicarbonate with a particle size distribution between 400 $\mu$m and 1200 $\mu$m |
| Silicate: | Amorphous Sodium Silicate ($SiO_2:Na_2O$; 2.0 ratio) |
| Sodium sulfate: | Anhydrous sodium sulfate |
| Citrate: | Tri-sodium citrate dihydrate of activity 86.4% with a particle size distribution between 425 $\mu$m and 850 $\mu$m |
| MA/AA: | Copolymer of 1:4 maleic/acrylic acid, average molecular weight about 70,000. |
| CMC: | Sodium carboxymethyl cellulose |
| Protease: | Proteolytic enzyme of activity 4 KNPU/g sold by NOVO Industries A/S under the tradename Savinase |
| Alcalase: | Proteolytic enzyme of activity 3 AU/g sold by NOVO Industries A/S |
| Cellulase: | Cellulytic enzyme of activity 1000 CEVU/g sold by NOVO Industries A/S under the tradename Carezyme |

-continued

| | |
|---|---|
| Amylase: | Amylolytic enzyme of activity 60 KNU/g sold by NOVO Industries A/S under the tradename Termamyl 60T |
| Lipase: | Lipolytic enzyme of activity 100 kLU/g sold by NOVO Industries A/S under the tradename Lipolase |
| Endolase: | Endoglunase enzyme of activity 3000 CEVU/g sold by NOVO Industries A/S |
| PB4: | Sodium perborate tetrahydrate of nominal formula $NaBO_2 \cdot 3H_2O \cdot H_2O_2$ |
| PB1: | Anhydrous sodium perborate monohydrate bleach of nominal formula $NaBO_2 \cdot H_2O_2$ |
| Percarbonate: | Sodium Percarbonate of nominal formula $2Na_2CO_3 \cdot 3H_2O_2$ |
| NOBS: | Nonanoyloxybenzene sulfonate in the form of the sodium salt. |
| TAED: | Tetraacetylethylenediamine |
| DTPMP: | Diethylene triamine penta (methylene phosphonate), marketed by Monsanto under the Trade name Dequest 2060 |
| Photoactivated: | Sulfonated Zinc Phthlocyanine encapsulated in dextrin soluble polymer |
| Brightener 1: | Disodium 4,4'-bis(2-sulphostyryl)biphenyl |
| Brightener 2: | Disodium 4,4'-bis(4-anilino-6-morpholinol-1.3.5-triazin-2-yl)amino)stilbene-2:2'-disulfonate. |
| HEDP: | 1,1-hydroxyethane diphosphonic acid |
| PVNO: | Polyvinylpyridine N-oxide |
| PVPVI: | Copolymer of polyvinylpyrolidone and vinylimidazole |
| SRP 1: | Sulfobenzoyl end capped esters with oxyethylene oxy and terephtaloyl backbone |
| SRP 2: | Diethoxylated poly (1,2 propylene terephtalate) short block polymer |
| Silicone antifoam: | Polydimethylsiloxane foam controller with siloxane-oxyalkylene copolymer as dispersing agent with a ratio of said foam controller to said dispersing agent of 10:1 to 100:1. |
| Alkalinity: | % weight equivalent of NaOH, as obtained using the alkalinity release test method described herein. |

In the following Examples all levels are quoted as % by weight of the composition:

EXAMPLE 1

The following granular laundry detergent compositions A and B of bulk density 750 g/liter were prepared in accord with the invention:

| | A | B | C | D |
|---|---|---|---|---|
| LAS | 5.61 | 4.76 | 5.5 | 6.5 |
| TAS | 1.86 | 1.57 | 2.1 | 1.5 |
| C45AS | 2.24 | 3.89 | 2.4 | 3.2 |
| C25AE3S | 0.76 | 1.18 | 0.8 | 1.3 |
| C45E7 | — | 5.0 | — | 2.5 |
| C25E3 | 5.5 | — | 2.5 | — |
| CEQ | 2.0 | 1.0 | — | — |
| QAS | — | 1.0 | 2.0 | 1.5 |
| Zeolite A | 19.5 | 19.5 | 16.5 | 16.5 |
| NaSKS-6/citric acid (79:21) | 10.6 | 10.6 | 10.6 | 6.9 |
| Carbonate | 21.4 | 21.4 | 16.5 | 19.3 |
| Bicarbonate | 2.0 | 2.0 | 2.0 | — |
| Silicate | 2.0 | — | — | 2.0 |
| Sodium sulfate | — | 14.3 | — | — |
| Percarbonare | 12.7 | — | 12.0 | — |
| TAED | 3.1 | — | 4.5 | — |
| DETPMP | 0.2 | 0.2 | 0.2 | 0.2 |
| HEDP | 0.3 | 0.3 | 0.3 | 0.3 |
| Protease | 0.85 | 0.85 | 0.85 | 0.85 |
| Lipase | 0.15 | 0.15 | 0.15 | 0.15 |
| Cellulase | 0.28 | 0.28 | 0.28 | 0.18 |
| Amylase | 0.1 | 0.1 | 0.1 | 0.1 |
| MA/AA | 1.6 | 1.6 | 1.0 | 2.2 |
| CMC | 0.4 | 0.4 | 0.7 | 0.7 |
| Photoactivated bleach (ppm) | 27 ppm | 27 ppm | 27 ppm | 27 ppm |
| Brightener 1 | 0.19 | 0.19 | 0.19 | 0.19 |
| Brightener 2 | 0.04 | 0.04 | 0.04 | 0.04 |
| Perfume | 0.3 | 0.3 | 0.3 | 0.3 |
| Silicone antifoam | 2.4 | 2.4 | 2.4 | 2.4 |
| Citric acid | 1.5 | 2.0 | 4.5 | 5.5 |
| Minors/misc to 100% | | | | |

EXAMPLE 2

The following detergent formulations, according to the present invention were prepared:

| | E | F | G |
|---|---|---|---|
| Blown Powder | | | |
| STPP | 14.0 | — | 14.0 |
| Zeolite A | — | 20.0 | — |
| C45AS | 9.0 | 6.0 | 8.0 |
| MA/AA | 2.0 | 4.0 | 2.0 |
| LAS | 6.0 | 8.0 | 9.0 |
| TAS | 2.0 | — | — |
| QAS II | 1.5 | 3.0 | 3.5 |
| Silicate | 7.0 | 8.0 | 8.0 |
| CMC | 1.0 | 1.0 | 0.5 |
| Brightener 2 | 0.2 | 0.2 | 0.2 |
| Soap | 1.0 | 1.0 | 1.0 |
| DTPMP | 0.4 | 0.4 | 0.2 |
| Spray On | | | |
| C45E7 | 2.5 | 2.5 | 2.0 |
| C25E3 | 2.5 | 2.5 | 2.0 |
| Silicone antifoam | 0.3 | 0.3 | 0.3 |
| Perfume | 0.3 | 0.3 | 0.3 |
| Dry additives | | | |
| Carbonate | 26.0 | 23.0 | 25.0 |
| Percarbonate | 18.0 | 18.0 | 10 |
| PB1 | — | — | 2.0 |
| TAED | 3.0 | 3.0 | 1.0 |
| Photoactivated bleach | 0.02 | 0.02 | 0.02 |
| Protease | 1.0 | 1.0 | 1.0 |
| Lipase | 0.4 | 0.4 | 0.4 |
| Amylase | 0.25 | 0.30 | 0.15 |
| Dry mixed sodium sulfate | 3.0 | 3.0 | 5.0 |
| Citric acid | 2.5 | 2.0 | 5.0 |
| Balance (Moisture & Miscellaneous) | 100.0 | 100.0 | 100.0 |
| Density (g/liter) | 630 | 670 | 670 |

EXAMPLE 3

The following nil bleach-containing detergent formulations of particular use in the washing of colored clothing, according to the present invention were prepared:

| | H | I |
|---|---|---|
| Blown Powder | | |
| Zeolite A | 15.0 | — |
| Sodium sulfate | — | — |
| LAS | 3.0 | — |
| QAS I | — | 1.5 |
| CEQ | 2.0 | 1.3 |

| | H | I |
|---|---|---|
| DTPMP | 0.4 | — |
| CMC | 0.4 | — |
| MA/AA | 4.0 | — |
| Agglomerates | | |
| C45AS | — | 11.0 |
| LAS | 6.0 | — |
| TAS | 3.0 | — |
| Silicate | 4.0 | — |
| Zeolite A | 10.0 | 13.0 |
| CMC | — | 0.5 |
| MA/AA | — | 2.0 |
| Carbonate | 9.0 | 7.0 |
| Spray On | | |
| Perfume | 0.3 | 0.5 |
| C45E7 | 4.0 | 4.0 |
| C25E3 | 2.0 | 2.0 |
| Dry additives | | |
| MA/AA | — | 3.0 |
| NaSKS-6 | — | 12.0 |
| Citric acid | 4.0 | 3.0 |
| Citrate | 10.0 | 8.0 |
| Bicarbonate | 7.0 | 5.0 |
| Carbonate | 8.0 | 7.0 |
| PVPVI/PVNO | 0.5 | 0.5 |
| Alcalase | 0.5 | 0.9 |
| Lipase | 0.4 | 0.4 |
| Amylase | 0.6 | 0.6 |
| Cellulase | 0.6 | 0.6 |
| Silicone antifoam | 5.0 | 5.0 |
| Dry additives | | |
| Sodium sulfate | 0.0 | 0.0 |
| Balance (Moisture and Miscellaneous) | 100.0 | 100.0 |
| Density (g/liter) | 700 | 700 |

EXAMPLE 4

The following detergent formulations, according to the present invention were prepared:

| | J | K | L | M |
|---|---|---|---|---|
| LAS | 12.0 | 12.0 | 12.0 | 10.0 |
| QAS | 0.7 | 1.0 | — | 0.7 |
| TFAA | — | 1.0 | — | — |
| C25E5/C45E7 | — | 2.0 | — | 0.5 |
| C45E3S | — | 2.5 | — | — |
| QAS II | 2.0 | 1.5 | 1.0 | 1.0 |
| STPP | 30.0 | 18.0 | 15.0 | — |
| Silicate | 9.0 | 7.0 | 10.0 | — |
| Carbonate | 15.0 | 10.5 | 15.0 | 25.0 |
| Bicarbonate | — | 10.5 | — | — |
| DTPMP | 0.7 | 1.0 | — | — |
| SRP 1 | 0.3 | 0.2 | — | 0.1 |
| MA/AA | 2.0 | 1.5 | 2.0 | 1.0 |
| CMC | 0.8 | 0.4 | 0.4 | 0.2 |
| Protease | 0.8 | 1.0 | 0.5 | 0.5 |
| Amylase | 0.8 | 0.4 | — | 0.25 |
| Lipase | 0.2 | 0.1 | 0.2 | 0.1 |
| Cellulase | 0.15 | 0.05 | — | — |
| Photoactivated bleach (ppm) | 70 ppm | 45 ppm | — | 10 ppm |
| Brightener 1 | 0.2 | 0.2 | 0.08 | 0.2 |
| percarbonate | 6.0 | 2.0 | — | — |
| NOBS | 2.0 | 1.0 | — | — |
| Citric acid | 3.5 | 5.0 | 3.0 | 2.0 |
| Balance (Moisture and Miscellaneous) | 100 | 100 | 100 | 100 |

EXAMPLE 5

The following detergent formulations, according to the present invention were prepared:

| | N | O | P |
|---|---|---|---|
| Blown Powder | | | |
| Zeolite A | 10.0 | 15.0 | 6.0 |
| Sodium sulfate | 19.0 | 5.0 | 7.0 |
| MA/AA | 3.0 | 3.0 | 6.0 |
| LAS | 10.0 | 8.0 | 10.0 |
| C45AS | 4.0 | 5.0 | 7.0 |
| QAS I | 2.0 | 4.0 | 1.0 |
| Silicate | — | 1.0 | 7.0 |
| Soap | — | — | 2.0 |
| Brightener 1 | 0.2 | 0.2 | 0.2 |
| Carbonate | 28.0 | 26.0 | 20.0 |
| DTPMP | — | 0.4 | 0.4 |
| Spray On | | | |
| C45E7 | 1.0 | 1.0 | 1.0 |
| Dry additives | | | |
| PVPVI/PVNO | 0.5 | 0.5 | 0.5 |
| Protease | 1.0 | 1.0 | 1.0 |
| Lipase | 0.4 | 0.4 | 0.4 |
| Amylase | 0.1 | 0.1 | 0.1 |
| Cellulase | 0.1 | 0.1 | 0.1 |
| NOBS | — | 6.1 | 4.5 |
| Percarbonate | 1.0 | 5.0 | 6.0 |
| Sodium sulfate | — | 6.0 | — |
| Citric acid | 2.5 | 2.5 | 2.0 |
| Balance (Moisture and Miscellaneous) | 100 | 100 | 100 |

EXAMPLE 6

The following high density and bleach-containing detergent formulations, according to the present invention were prepared:

| | Q | R |
|---|---|---|
| Blown Powder | | |
| Zeolite A | 15.0 | 15.0 |
| Sodium sulfate | 0.0 | 0.0 |
| LAS | 8.0 | 3.0 |
| QAS | — | 1.5 |
| CEQ | 2.0 | — |
| DTPMP | 0.4 | 0.4 |
| CMC | 0.4 | 0.4 |
| MA/AA | 4.0 | 2.0 |
| Agglomerates | | |
| LAS | 4.0 | 4.0 |
| TAS | 2.0 | 1.0 |
| Silicate | 3.0 | 4.0 |
| Zeolite A | 8.0 | 8.0 |
| Carbonate | 8.0 | 6.0 |

-continued

|  | Q | R |
|---|---|---|
| Spray On | | |
| Perfume | 0.3 | 0.3 |
| C45E7 | 2.0 | 2.0 |
| C25E3 | 2.0 | — |
| Dry additives | | |
| Citric acid | 2.0 | 3.0 |
| Citrate | 5.0 | 2.0 |
| Bicarbonate | — | — |
| Carbonate | 8.0 | 10.0 |
| TAED | 6.0 | 5.0 |
| Percarbonate | 14.0 | 10.0 |
| Polyethylene oxide of MW 5,000,000 | — | 0.2 |
| Bentonite clay | — | 10.0 |
| Protease | 1.0 | 1.0 |
| Lipase | 0.4 | 0.4 |
| Amylase | 0.6 | 0.6 |
| Cellulase | 0.6 | 0.6 |
| Silicone antifoam | 5.0 | 5.0 |
| Dry additives | | |
| Sodium sulfate | 2.0 | 0.0 |
| Balance (Moisture and Miscellaneous) | 100.0 | 100.0 |
| Density (g/liter) | 850 | 850 |

EXAMPLE 7

The following high density detergent formulations, according to the present invention were prepared:

|  | S | T |
|---|---|---|
| Agglomerate | | |
| C45AS | 11.0 | 14.0 |
| QAS I | 1.0 | 2.0 |
| CEQ | 3.0 | — |
| Zeolite A | 15.0 | 6.0 |
| Carbonate | 4.0 | 8.0 |
| MA/AA | 4.0 | 2.0 |
| CMC | 0.5 | 0.5 |
| DTPMP | 0.4 | 0.4 |
| Spray On | | |
| C25E5 | 5.0 | 5.0 |
| Perfume | 0.5 | 0.5 |
| Dry Adds | | |
| Citric acid | 1.5 | 2.0 |
| HBDP | 0.5 | 0.3 |
| SKS 6 | 13.0 | 10.0 |
| Citrate | 3.0 | 1.0 |
| TAED | 5.0 | 7.0 |
| Percarbonate | 20.0 | 20.0 |
| SRP 1 | 0.3 | 0.3 |
| Protease | 1.4 | 1.4 |
| Lipase | 0.4 | 0.4 |
| Cellulase | 0.6 | 0.6 |
| Amylase | 0.6 | 0.6 |
| Silicone antifoam | 5.0 | 5.0 |
| Brightener 1 | 0.2 | 0.2 |
| Brightener 2 | 0.2 | — |
| Balance (Moisture and Miscellaneous) | 100 | 100 |
| Density (g/liter) | 850 | 850 |

What is claimed is:

1. A cosmetic article for cleansing body surfaces, the article comprising:

a sealed pouch formed with at least one water permeable wall; and an effervescent cleanser composition in an anhydrous dry solid form positioned within the pouch, the composition comprising from about 0.1 to about 3% by weight of the solid of a fragrance or botanical extract deposited upon the anhydrous dry solid and from about 0.01 to about 30% by weight of the solid of an anti-aging active selected from the group consisting of vitamins, retinoids and mixtures thereof.

2. A method for imparting a pleasant sensory feel to skin comprising wetting with water a cosmetic cleansing article, generating foam from the article and wiping skin surfaces with the wetted article, the article comprising:

a sealed pouch formed with at least one water permeable wall; and an effervescent cleanser composition in an anhydrous dry solid form positioned within the pouch, the composition comprising from about 0.1 to about 3% by weight of the solid of a fragrance or botanical extract deposited upon the anhydrous dry solid.

3. A cosmetic article for cleansing body surfaces, the article comprising a sealed pillow plumped by effervescent generated carbon dioxide and exuding lather and an emollient.

4. The article according to claim 3 wherein the effervescent generated carbon dioxide, the exuded lather and the emollient arise from a composition stored withing the pillow comprising from about 1 to about 80% of an alkaline material, from about 0.5 to about 80% of an acid material, from about 0.1 to about 30% of a surfactant and from about 0.01 to about 30% of an emollient by weight of the composition.

* * * * *

UNITED STATES PATENT AND TRADEMARK OFFICE
CERTIFICATE OF CORRECTION

PATENT NO.     : 6,610,312 B2
DATED          : August 26, 2003
INVENTOR(S)    : Linda Farrell et al.

It is certified that error appears in the above-identified patent and that said Letters Patent is hereby corrected as shown below:

Delete title page and therefore substitute the title page as shown in the attached page.

Delete specification, cols. 1-32 and substitute therefore specification cols. 1-10

Signed and Sealed this

Fifteenth Day of February, 2005

JON W. DUDAS
*Director of the United States Patent and Trademark Office*

(12) United States Patent
Farrell et al.

(10) Patent No.: US 6,610,312 B2
(45) Date of Patent: *Aug. 26, 2003

(54) COSMETIC EFFERVESCENT CLEANSING PILLOW

(75) Inventors: Linda Farrell, Stratford, CT (US); Craig Stephen Slavtcheff, Guilford, CT (US); Alexander Paul Znaiden, Trumbull, CT (US); Paul Vinski, Danbury, CT (US)

(73) Assignee: Unilever Home & Personal Care USA, Division of Conopco, Inc., Greenwich, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/783,777

(22) Filed: Feb. 15, 2001

(65) Prior Publication Data

US 2001/0026792 A1 Oct. 4, 2001

Related U.S. Application Data

(62) Division of application No. 09/532,767, filed on Mar. 22, 2000, now Pat. No. 6,217,854, which is a division of application No. 09/130,981, filed on Aug. 7, 1998, now Pat. No. 6,063,390.

(51) Int. Cl.[7] ............... A61K 7/42; A61K 9/70; A61K 7/46; A61L 9/04; A01N 25/34
(52) U.S. Cl. ............... 424/401; 424/43; 424/44; 424/59; 424/402; 424/404; 424/443; 512/4; 510/130; 510/135
(58) Field of Search ............... 424/401, 402, 424/404, 409, 443, 43, 44, 59; 512/4; 510/130, 135

(56) References Cited

U.S. PATENT DOCUMENTS

| | | |
|---|---|---|
| 1,808,834 A | 6/1931 | Busch, Sr. |
| 3,242,093 A | 3/1966 | Compton et al. |
| 4,025,628 A | 5/1977 | Dewey et al. |
| 4,234,442 A | 11/1980 | Cornelissens |
| 4,272,393 A | 6/1981 | Gergely |
| 4,291,685 A | 9/1981 | Taelman |
| 4,311,606 A | 1/1982 | Kaeser |
| 4,515,703 A | 5/1985 | Haq |
| 4,592,855 A | 6/1986 | Gioffre et al. |
| 4,600,620 A | 7/1986 | Lloyd et al. |
| 4,601,938 A | 7/1986 | Deacon et al. |
| 4,603,069 A | 7/1986 | Haq et al. |
| 4,643,939 A | 2/1987 | Sugiyama et al. |
| 4,666,707 A | 5/1987 | Eguchi et al. |
| 4,745,021 A | 5/1988 | Ping, III et al. |
| 4,791,097 A | 12/1988 | Walele et al. |
| 4,808,322 A | 2/1989 | McLaughlin |
| 4,852,201 A | 8/1989 | Wundrock et al. |
| 4,886,387 A | 12/1989 | Goldberg et al. |
| 4,941,990 A | 7/1990 | McLaughlin |
| 5,006,339 A | 4/1991 | Bargery et al. |
| 5,026,551 A | 6/1991 | Yorozu et al. |
| 5,041,233 A | 8/1991 | Kutny et al. |
| 5,100,674 A | 3/1992 | Ser et al. |
| 5,198,198 A | 3/1993 | Gladfelter et al. |
| 5,306,439 A | 4/1994 | Lockhart |
| 5,338,476 A | 8/1994 | Pancheri et al. |
| 5,342,535 A | 8/1994 | Ramirez et al. |
| 5,352,387 A | 10/1994 | Rahman et al. |
| 5,431,841 A | 7/1995 | Lockhart |
| 5,560,873 A | 10/1996 | Chen et al. |
| 5,578,562 A | 11/1996 | Lockhart |
| 5,605,749 A | 2/1997 | Pike et al. |
| 5,607,681 A | 3/1997 | Galley et al. |
| 5,683,976 A | 11/1997 | Colurciello, Jr. et al. |
| 5,714,451 A | 2/1998 | Brouwer et al. |
| 5,718,729 A | 2/1998 | Harris |
| 5,720,949 A | 2/1998 | Davis |
| 5,804,546 A | 9/1998 | Hall |
| 5,955,057 A | 9/1999 | Maunder et al. |
| 6,063,390 A | 5/2000 | Farrell et al. |
| 6,093,218 A | 7/2000 | Hall et al. |
| 6,121,215 A | 9/2000 | Rau |

FOREIGN PATENT DOCUMENTS

| | | |
|---|---|---|
| DE | 19745964 | 12/1996 |
| EP | 343070 | 5/1989 |
| EP | 343069 | 11/1989 |
| EP | 423015 | 4/1991 |
| EP | 0 806 201 | 5/1996 |
| GB | 2 118 961 | 4/1982 |
| JP | 62045519 | 2/1987 |
| JP | 10245075 | 9/1998 |
| WO | 97/43366 | 11/1997 |
| WO | 98/42303 | 10/1998 |

OTHER PUBLICATIONS

International Search Report, Oct. 11, 1999.

*Primary Examiner*—Jose G. Dees
*Assistant Examiner*—Marina Lamm
(74) *Attorney, Agent, or Firm*—Milton L. Honig

(57) ABSTRACT

A wiping article is provided which includes an effervescent cleanser composition held within a pouch formed from a first and second substrate sheet. At least one of the substrate sheets must be water permeable. The effervescent composition is an intimate mixture of an acid material such as citric acid and an alkaline material such as sodium bicarbonate. Water contact causes the combination to effervesce. A dry surfactant such as sodium cocoyl isethionate in contact with the water and effervescing carbon dioxide results in a highly pleasant sudsing system. Skin benefit agents may be included within the composition. The effervescent action may improve deposition of the skin benefit agents onto the skin.

4 Claims, No Drawings

COSMETIC EFFERVESCENT CLEANSING PILLOW

This is a Divisional application of Ser. No. 09/532,767 filed Mar. 22, 2000 now a U.S. Pat. No. 6,217,854, which is a Divisional application of Ser. No. 09/130,981, filed Aug. 7, 1998 now U.S. Pat. No. 6,063,390.

BACKGROUND OF THE INVENTION

1. Field of the Invention

The invention concerns an effervescent foaming wipe article for body cleansing that imparts a pleasant sensory feel to a user's skin.

2. The Related Art

Classically the process of cleansing skin or other articles has employed a surfactant composition. Sometimes an implement has joined the composition. Implements such as sachets serve a multi-purpose. One function is as a delivery package for the surfactant. Sachets may also assist in generating foam. They also function as an abrasive assisting in the cleansing function.

An early example of cleansing pad technology is found in U.S. Pat. No. 1,808,834 (Busch Sr.). A fabric pouch is disclosed surrounding a cleansing composition mainly consisting of calcium and sodium carbonate.

U.S. Pat. No. 4,234,442 (Cornelissens) describes a sachet which can consist of a water permeable material filled with an acidic and an alkaline constituent. Adipic, succinic and glutaric acids exemplify the acidic constituent. Sodium bicarbonate and carbonate represent the alkaline ingredient.

U.S. Pat. No. 4,272,393 (Gergely) describes a cleaning article formed of a porous flexible substrate, especially a cellulosic paper, impregnated with detergent and a gas-generating system. The latter is formed by separating an acidic component such as citric acid from a basic component such as sodium carbonate in two separate areas of the substrate.

U.S. Pat. No. 4,515,703 (Haq), U.S. Pat. No. 4,600,620 (Lloyd et al.) and U.S. Pat. No. 4,603,069 (Haq et al.) all describe wiping articles impregnated with surfactant. These do not contain any effervescent ingredients.

WO 97/43366 (Askew et al.) reports an effervescent system to improve dispensability of granular laundry detergent powders into wash water of automatic washing machines. Citric acid and bicarbonate combinations are employed to generate effervescence.

It is an object of the present invention to provide a cleansing cloth containing an effervescent system activated by contact with water.

Another object of the present invention is to provide a cleansing cloth containing an effervescent system activated by contact with water to generate carbon dioxide which expands the lathering of cleanser components of the cloth.

Still a further object of the invention is to provide a cleansing cloth which imparts a pleasant sensory feel to skin during and after use.

It is to be noted that the subsequently described invention is broader than the objects or technical problems it is directed to solve.

SUMMARY OF THE INVENTION

A cosmetic article is provided for cleansing body surfaces, the article including:

a pouch formed of first and second sheets, at least one being water permeable, the first and second sheets defining a pouch between them, the pouch being sealed along all its perimeter; and an effervescent cleanser composition in the form of an anhydrous dry solid being positioned within the pouch, the composition including:

(i) from about 1 to about 80% of an alkaline material;
(ii) from about 0.5 to about 80% of an acid material; and
(iii) from about 0.1 to about 30% of a solid surfactant.

Also provided is a method for cleansing skin involving wetting with water a cosmetic cleansing article, generating foam from the article and wiping skin surfaces with the wetted article, the article being the pouch with effervescent cleanser composition delineated above.

DETAILED DESCRIPTION OF THE INVENTION

Cosmetic wiping articles of the present invention when contacted with water billow to many times (more than 10 but often more than 40 times) their dry size when activated by water. The effervescent cleansing system exudes copious amounts of lather. A plumped "pillow" arises from the effervescent action. By careful control of the acidic and alkaline components, a squeaky clean rinsed feeling is felt on a user's skin.

A first essential component of compositions within the pouch is that of an acidic material. Suitable for this purpose are any acids present in dry solid form. Especially appropriate are $C_2$–$C_{20}$ organic mono- and poly- carboxylic acids and especially alpha- and beta- hydroxycarboxylic acids; $C_2$–$C_{20}$ organophosphorus acids such as phytic acid; $C_2$–$C_{20}$ organosulfur acids such as toluene sulfonic acid; and peroxides such as hydrogen peroxide. Typical hydroxycarboxylic acids include adipic, glutaric, succinic, tartaric, malic, maleic, lactic, salicylic and citric acids as well as acid forming lactones such as gluconolactone and glucarolactone. Most preferred is citric acid. Also suitable as acid material may be encapsulated acids. Typical encapsulating material may include water soluble synthetic or natural polymers such as polyacrylates (e.g. encapsulating polyacrylic acid), cellulosic gums, polyurethane and polyoxyalkylene polymers. By the term "acid" is meant any substance which when dissolved in deionized water at 1% concentration will have a pH of less than 7, preferably less than 6.5, optimally less than 5. These acids preferably at 25° C. are in solid form, i.e. having melting points no less than 25° C. Concentrations of the acid should range from about 0.5 to about 80%, preferably from about 10 to about 65%, optimally from about 20 to about 45% by weight of the total composition.

A second essential component of compositions within the pouch is that of an alkaline material. The alkaline material is a substance which can generate a gas such as carbon dioxide, nitrogen or oxygen, i.e. effervesce, when contacted with water and the acidic material. Suitable alkaline materials are anhydrous salts of carbonates and bicarbonates, alkaline peroxides (e.g. sodium perborate and sodium percarbonate) and azides (e.g. sodium azide). Preferably the alkaline material is sodium or potassium bicarbonate. Amounts of the alkaline material may range from about 1 to about 80%, preferably from about 5 to about 49%, more preferably from about 15 to about 40%, optimally from about 25 to about 35% by weight of the total composition.

By the term "anhydrous" is meant the presence of no more than 5%, preferably no more than 3.5% and optimally no more than 1% water by weight of the total composition. Water of hydration is not considered to be water for purposes of the anhydrous definition. However, it is preferred to minimize, preferably to eliminate any water of hydration.

Advantageously the combined amount of acidic and alkaline materials will be at least about 1.5%, preferably from about 40 to about 95%, optimally from about 60 to about 80% by weight of the total composition.

A third necessary component of compositions according to the present invention is that of a dry surfactant, preferably a dry surfactant solid at 20° C. Most suitable for the present invention is sodium cocoyl isethionate. Other useful surfactants include sodium methyl cocoyl taurate and sodium lauryl sulfate. Surfactants may be of the anionic, cationic, nonionic, amphoteric, zwitterionic varieties and combinations thereof. Amounts of the dry surfactant may range from about 0.1 to about 30%, preferably from about 1 to about 30%, optimally from about 8 to about 15% by weight of the total composition.

A variety of skin benefit agents may be included to improve afterfeel properties. Advantageously these substances will be available as anhydrous dry powders. Alternatively these substances may be liquids deposited upon or into a powdered substrate (e.g. sodium bicarbonate or zeolite) to achieve a resultant dry flowing powder. Within the skin benefit agent scope are several categories of materials. These include emollients, antiaging actives, antibacterials and fungicides, skin lighteners, sunscreens and combinations thereof. Amounts of the skin benefit agents may range from about 0.001 to about 30%, preferably from about 0.1 to about 20%, more preferably from about 0.5 to about 10%, optimally between about 1 and about 5% by weight of the total composition.

Emollients may be in the form of natural or synthetic esters, silicone oils, hydrocarbons, starches, fatty acids and mixtures thereof. Typically the emollient may range in concentration from about 0.1 to about 35% by weight of the total composition.

Silicone oils may be divided into the volatile and non-volatile variety. The term "volatile" as used herein refers to those materials which have a measurable vapor pressure at ambient temperature. Volatile silicone oils are preferably chosen from cyclic or linear polydimethylsiloxanes containing from 3 to 9, preferably from 4 to 5, silicon atoms.

Linear volatile silicone materials generally have viscosities less than about 5 centistokes at 25° C. while cyclic materials typically have viscosities of less than about 10 centistokes.

Nonvolatile silicone oils useful as an emollient material include polyalkyl siloxanes, polyalkylaryl siloxanes and polyether siloxane copolymers. The essentially non-volatile polyalkyl siloxanes useful herein include, for example, polydimethyl siloxanes with viscosities of from about 5 to about 100,000 centistokes at 25° C. Among the preferred non-volatile emollients useful in the present compositions are the polydimethyl siloxanes having viscosities from about 10 to about 400 centistokes at 25° C.

Among the ester emollients are:

(1) Alkenyl or alkyl esters of fatty acids having 10 to 20 carbon atoms. Examples thereof include isoarachidyl neopentanoate, isononyl isonanonoate, oleyl myristate, oleyl stearate, and oleyl oleate.

(2) Ether-esters such as fatty acid esters of ethoxylated fatty alcohols.

(3) Polyhydric alcohol esters. Ethylene glycol mono and di-fatty acid ester, diethylene glycol mono- and di-fatty acid esters, polyethylene glycol (200–6000) mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

(4) Wax esters such as beeswax, spermaceti, myristyl myristate, stearyl stearate and arachidyl behenate.

(5) Sterols esters, of which cholesterol fatty acid esters are examples thereof.

(6) Triglycerides such as sunflower seed oil, maleated sunflower seed oil, borage seed oil and safflower oil.

Hydrocarbons suitable as emollients include petrolatum, mineral oil, isoparaffins and hydrocarbon waxes such as polyethylene.

Starches are also suitable emollients. Typical of this class is tapioca and arabinogalactan.

Fatty acids may also be suitable as emollients. The fatty acids normally have from 10 to 30 carbon atoms. Illustrative of this category are pelargonic, lauric, myristic, palmitic, stearic, isostearic, hydroxystearic, oleic, linoleic, riconleic, arachidic, behenic and erucic acids.

Antiaging actives are also useful as skin benefit agents. Included within this category are vitamins, retinoids and combinations thereof. Amounts of these materials may range from about 0.001 to about 20% by weight of the total composition. Suitable vitamins include ascorbic acid, Vitamin $B_6$, Vitamin $B_{12}$, tocopherol as well as salts and $C_1$–$C_{20}$ esters thereof. Suitable retinoids include retinoic acid as well as its $C_1$–$C_{22}$ esters and salts, retinal and $C_1$–$C_{22}$ fatty esters of retinol including retinyl linoleate.

Another class of antiaging actives are the alpha- and beta-hydroxycarboxylic acids and salts thereof. Representative of this group are glycolic acid, lactic acid, malic acid, hydroxyoctanoic acid and mixtures of these as well as their salts. Suitable salts are the alkalimetal, ammonium and $C_1$–$C_{10}$ alkanol ammonium salts.

Antibacterials and fungicidals may also be included as skin benefit agents. Representative of these categories are triclosan, tricloban, hexetidene, chlorhexadene, gluconates, zinc salts (e.g. zinc citrate and zinc phenolsulfonate) and combinations thereof.

Skin lighteners may also be included under the skin benefit agents. Typical of this category are niacinamide, kojic acid, arbutin, vanillin, ferulic acid and esters thereof, resorcinol, hydroquinone, placental extract and combinations thereof.

Sunscreens may also be included as skin benefit agents. Particularly preferred are such materials as ethylhexyl p-methoxycinnamate, available as Parsol® MCX, and benzophenone-3, also known as Oxybenzone. Inorganic sunscreen actives may be employed such as microfine titanium dioxide, polyethylene and various other polymers. Amounts of the sunscreen agents will generally range from 0.1 to 30%, preferably from 2 to 20%, optimally from 4 to 10% by weight.

Adjunct functional agents may also be incorporated into compositions of the present invention. These include electrolytes, thickeners and mixtures thereof. Amounts of these substances may range from about 0.1 to about 20%, preferably from about 0.3 to about 10%, optimally between about 0.5 and about 5% by weight of the total composition.

Electrolytes may be selected from alkali, alkaline earth or ammonium salts of phosphates, silicates, halides, sulphates and mixtures thereof. Typical phosphates are potassium polymetaphosphate, sodium tripolyphosphate, sodium tetrapyrophosphate, sodium or potassium pyrophosphate and sodium hexametaphosphate. Most preferred is potassium polymetaphosphate available as Lipothix 100B® which is a 70:30 mixture of potassium polymetaphosphate and sodium bicarbonate, available from Lipo Chemicals, Inc., Paterson, N.J. Preferred sulphates are the magnesium sulphates.

Thickeners which may improve afterfeel properties on skin include inorganic or organic substances. A particularly preferred inorganic thickener is sodium magnesium silicate commercially available as Optigel SH®. Organic thickeners include alginic acid as well as sodium and calcium alginates, sodium carboxymethyl cellulose, hydroxypropyl methylcellulose, hydroxypropyl cellulose, hydroxyethyl cellulose and combinations thereof. Most preferred is alginic acid commercially available as Kelacid® from Sud-Chemie Rheologicals, Louisville, Ky. Alginic acid is highly effective at removing the slimy feel associated with deposits of alkaline material which are not fully rinsed away from the skin. Amounts of the thickener may range from about 0.1 to about 20%.

Polysaccharides useful in this invention are dry solid anhydrous substances such as sorbitol, sugars, (such as trehalose) starches, modified starches (e.g. aluminum octenyl succinate) and mixtures thereof. Most preferred is sorbitol.

Deposition aids may also be incorporated in compositions of the present invention. These assist in depositing skin benefit agents onto the skin surface. Particularly effective are cationic monomers and polymers for this purpose. Illustrative are the following:

| | |
|---|---|
| Lauryltrimethylammonium chloride | (Laurtrimonium chloride); |
| Stearyltri(2-hydroxyethyl)ammonium chloride | (Quaternium-16); |
| Lauryldimethylbenzylammonium chloride | (Lauralkonium chloride); |
| Oleyldimethylbenzylammonium chloride | (Olealkonium chloride); |
| Dilauryldimethylammonium chloride | (Dilauryldimonium chloride |
| Cetyldimethylbenzylammonium chloride | (Cetalkonium chloride); |
| Dicetyldimethylammonium chloride | (Dicetyldimonium chloride); |
| Laurylpyridinium chloride | (Laurylpyridinium chloride); |
| Cetylpyridinium chloride | (Cetylpyridinium chloride); |
| N-(soya alkyl)-N,N,N-trimethyl-ammonium chloride | (Soyatrimonium chloride); |
| Polydiallyldimethylammonium chloride | (Polyquaternium-6); |
| Diallydimethylammonium salt copolymerized with acrylamide | (Polyquaternium-7); |
| Guar hydroxypropyltrimonium chloride | (Guar hydroxypropyl-trimonium chloride); |
| Copolymer of N-vinyl-pyrrolidone and N,N-dimethylaminoethylmethacrylate quaternized with dimethylsulfate | (Polyquaternium-11); |
| Copolymer of acrylamide and N,N-dimethylaminoethyl methacrylate, quaternized with dimethyl sulfate | (Polyquaternium-5); |
| Cationic hydroxyethylcellulosics | (Polyquaternium-10); |
| Cationic hydroxyethylcellulosics | (Polyquaternium-24); |
| Cetyltrimethylammonium chloride | (Cetrimonium chloride); |
| Decyldimethyloctylammonium chloride | (Quaternium-24); |
| Myristyltrimethylammonium chloride | (Mytrimonium chloride); |
| Polyoxyethylene (2)-cocomonium chloride | (PEG-2 Cocomonium chloride); |
| Methylbis(2-hydroxyethyl) cocoammonium chloride | (PEG-2 Cocoyl Quaternium-4); |
| Methylpolyoxyethylene-(15) cocoammonium chloride | (PEG-15 Cocoyl Quaternium-4); |
| Methylbis(2-hydroxyethyl) octadecyl ammonium chloride | (PEG-2 Stearyl Quaternium-4); |
| Methylpolyoxyethylene-(15) octadecylammonium chloride | (PEG-15 Stearyl Quaternium-4); |
| Methylbis(2-hydroxyethyl)-oleylammonium chloride | (PEG-2 Oleyl Quaternium-4); |
| Methylpolyoxyethylene-(15) oleylammonium chloride | (PEG-15 Oleyl Quaternium-4); |

The names in parenthesis are given by the Cosmetic, Toiletry and Fragrance Association, Inc. in the CTFA Cosmetic Ingredient Dictionary. Most preferred for purposes of this invention are cationic guar gums such as Jaguar C13S® which is guar hydroxypropyltrimonium chloride. Amounts of the deposition aid may range from about 0.01 to about 1%, preferably from about 0.05 to about 0.5%, optimally from about 0.1 to about 0.3% by weight.

Advantageously an emotive agent such as a fragrance and/or botanical extract are included with the effervescent cleansing composition. Fragrances and botanicals are often liquids. For this reason it is necessary to uniformly distribute and allow absorption of liquid components into the solid powder. One method of best achieving this is to spray these liquids onto the solids. Amounts of the fragrance and/or botanicals combined may be at levels from abut 0.1 to about 3%, preferably from 0.5 to 2%, optimally from 0.8 to 1.5% by weight of the total composition.

The term "fragrance" is defined as a mixture of odoriferous components, optionally mixed with a suitable solvent diluent or carrier, which is employed to impart a desired odor. Particular preferred odoriferous components are cyclic and acyclic terpenes and terpenoids. These materials are based upon isoprene repeating units. Examples include alpha and beta pinene, myrcene, geranyl alcohol and acetate, camphene, dl-limonene, alpha and beta phellandrene, tricyclene, terpinolene, allocimmane, geraniol, nerol, linanool, dihydrolinanool, citral, ionone, methyl ionone, citronellol, citronellal, alpha terpineol, beta terpineol, alpha fenchol, borneol, isoborneol, camphor, terpinen-1-ol, terpin-4-ol, dihydroterpineol, methyl chavicol, anethole, 1,4 and 1,8 cineole, geranyl nitrile, isobornyl acetate, linalyl acetate, caryophyllene, alpha cedrene, guaiol, patchouli alcohol, alpha and beta santalol and mixtures thereof. Botanicals of particular use in the present invention include yarrow, chamomile, jasmine, lavender, horse chestnut, sage, thyme, yucca, coltsfoot and mixtures thereof.

Preservatives can desirably be incorporated into the cosmetic compositions of this invention to protect against the growth of potentially harmful microorganisms. Suitable traditional preservatives for compositions of this invention are alkyl esters of para-hydroxybenzoic acids. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are phenoxyethanol, methyl paraben, propyl paraben, imidazolidinyl urea, sodium dehydroacetate and benzyl alcohol. The preservatives should be selected having regard for the sue of the composition and possible incompatibilities between the preservatives and other ingredients in the emulsion. Preservatives are preferably employed in amounts ranging from 0.01% to 2% by weight of the composition.

Natural vegetable materials from renewable resources are often desirable in cosmetic compositions. For instance, cosmetic compositions of the present invention may include beta-glucan derived from oats, commercially available under the trademark Microat SF from Nurture Inc., Missoula, Mont.

Colorants may also be included in compositions of the present invention. These substances may range from about 0.05 to about 5%, preferably between 0.1 and 3% by weight.

Effervescent cleansing compositions of this invention will be placed within a pouch formed between a first and second flexible substrate sheet, preferably at least one of these being a flexible sheet. At least one of the sheets must be water permeable, most preferably both sheets should have water permeability. For definitional purposes, first and second sheets can be folded-over panels of a single unitary sheet. Suitable materials for forming sheets may be rayon, polyester, polyethylene, polypropylene, cotton or any combination thereof. These sheets may be woven or non-woven. Most preferred is a non-woven rayon. Cellulosic paper fiber substrates are best not employed because of their insufficient wet-strength although they may be blended with other fibers referenced above; it is important that the substrate sheets are not readily torn open through consumer rubbing of the article. Unlike laundry sachet articles, pouches of the present invention should not rupture to allow dispersion of their granular contents into wash water. Rather it is intended for all cleanser composition components to exit by dissolution through the permeable walls of the pouch.

Skin surfaces against which articles of the present invention are useful include face, body, scalp, axilla and even legs/feet. When the article is a foot cleanser, it would be advantageous for the pouch on one of its sides to be coarse while the second of the sheets may be soft and gentle. An abrasive non-woven flexible sheet in a foot cleanser product is useful for rubbing against calluses while the second sheet of the pouch remains smooth.

Articles according to the present invention may be formed in the following manner. Constituents of the effervescent cleansing composition are placed into a dry mill or similar apparatus and blended until a uniformally distributed powder results. Thereafter, fragrance/botanical component as a Phase B is sprayed into the dry mill with concurrent agitation of the powdered composition.

A continuous roll of first substrate sheet is unwound from a source roll over a moving conveyer belt. The effervescent cleansing composition is placed into a hopper positioned over the conveyer belt. A discrete charge of powdered composition is regularly placed on the first substrate sheet at a location directly under a nozzle of the hopper. A second substrate sheet is then in register placed over that of the loaded first substrate sheet. At this point all four corners defining a rectangle or square are sealed in register trapping the effervescent cleansing composition within. Cutters then separate one sealed section from another thereby forming the wiping article. One or more of the wiping articles are then packaged within a moisture impermeable outer package such as a laminated foil bag to prevent activation of the effervescent system during storage.

Ultrasonic welding may be employed as an alternative to heat-sealing of the first and second substrates together. Thread stitching, glue application or other closure mechanisms may also be utilized.

Except in the operating and comparative examples, or where otherwise explicitly indicated, all numbers in this description indicating amounts of material are to be understood as modified by the word "about".

The term "comprising" is meant not to be limiting to any subsequently stated elements but rather to encompass non-specified elements of major or minor functional importance. In other words the listed steps, elements or options need not be exhaustive.

The following examples will more fully illustrate embodiments of this invention. All parts, percentages and proportions referred to herein and in the appended claims are by weight unless otherwise indicated.

EXAMPLE 1

An effervescent cleansing composition was prepared according to the formulation reported in Table I. Phase A was dry blended in a high speed shearing mixer. Fragrance was then sprayed onto the resultant powder as a Phase B. Three grams of the resultant powder were then placed into a two inch by three inch pouch formed of non-woven rayon. All sides were closed by double stitching with thread.

TABLE I

| INGREDIENT | WEIGHT % |
| --- | --- |
| PHASE A | |
| Sodium Bicarbonate | 34.5 |
| Citric Acid (Anhydrous) | 40.4 |
| Sodium Cocoyl Isethionate (Powder) | 11.6 |
| Sodium Sesquicarbonate | 5.0 |
| Lipothix 100B ® (Potassium Polymetaphosphate/Bicarbonate 70:30) | 0.5 |
| Optigel SH ® (Sodium Magnesium Silicate) | 1.0 |
| Kelacid ® (Alginic Acid) | 1.0 |
| Sorbitol | 5.0 |
| PHASE B | |
| Fragrance | 1.0 |

EXAMPLE 2

Another effervescent cleansing composition was prepared according to the formulation reported in Table II.

TABLE II

| INGREDIENT | WEIGHT % |
| --- | --- |
| PHASE A | |
| Sodium Bicarbonate | 32.3 |
| Citric Acid (Anhydrous) | 41.1 |
| Sodium Cocyl Isethionate (Powder) | 11.6 |
| Sodium Sesquicarbonate | 5.0 |
| Lipothix 100B ® (Potassium Polymetaphosphate/Bicarbonate 70:30) | 0.5 |
| Optigel SH ® (Sodium Magnesium Silicate) | 1.0 |
| Kelacid ® (Alginic Acid) | 1.0 |
| Sorbitol | 5.0 |
| Laracare A200 ® (Arabinogalactan) | 1.0 |
| Ascorbic Acid | 0.5 |
| PHASE B | |
| Fragrance | 1.0 |

EXAMPLE 3

A face cleansing effervescent composition was prepared according to the formulation reported in Table III.

TABLE III

| INGREDIENT | WEIGHT % |
| --- | --- |
| PHASE A | |
| Sodium Bicarbonate | 33.6 |
| Citric Acid (Anhydrous) | 39.0 |
| Sodium Cocyl Isethionate (Powder) | 3.0 |

TABLE III-continued

| INGREDIENT | WEIGHT % |
|---|---|
| Sodium Methyl Cocoyl Taurate | 6.0 |
| Sodium Lauryl Sulfate | 2.5 |
| Sodium Sesquicarbonate | 5.0 |
| Lipothix 100B ® (Potassium Polymetaphosphate/Bicarbonate 70:30) | 0.5 |
| Optigel SH ® (Sodium Magnesium Silicate) | 2.0 |
| Tapioca | 5.5 |
| Methyl Gluceth 20-Benzoate | 2.0 |
| Guar Hydroxypropyl Trimonium Chloride | 0.25 |
| PHASE B | |
| Fragrance | 0.65 |

EXAMPLE 4

A still further effervescent cleansing composition according to the present invention may be prepared according to the formulation reported under Table IV. Phase A is prepared by dry mixing of the ingredients in a high speed shear mixer. Three grams of resultant powder are placed into a two inch by three inch pouch formed of non-woven cotton polyester (50:50). The mesh size of the pouch walls is sufficient to allow transfer of dissolved ingredients. All sides of the pouch are welded by ultrasonic heat to insure against powder escaping from the pouch.

TABLE IV

| INGREDIENT | WEIGHT % |
|---|---|
| PHASE A | |
| Potassium Bicarbonate | 29.5 |
| Lactic Acid (Anhydrous) | 45.4 |
| Sodium Sulfosuccinate | 11.6 |
| Sodium Sesquicarbonate | 5.0 |
| Lipothix 100B ® (Potassium Polymetaphosphate/Bicarbonate 70:30) | 0.5 |
| Optigel SH ® (Sodium Magnesium Silicate) | 1.0 |
| Kelacid ® (Alginic Acid) | 1.0 |
| Sorbitol | 5.0 |
| PHASE B | |
| Fragrance | 1.0 |
| Licorice Extract | 0.1 |

EXAMPLE 5

Still another effervescent cleansing composition is prepared according to the formulation reported in Table V. The ingredients are dry blended in a high speed shearing mixer. Fragrance and herbal extract are sprayed onto the powder and further blended to achieve homogeneity. Three grams of the resultant powder are placed into a two inch by three inch pouch formed of non-woven polypropylene. All sides are closed by convection heat sealing along the perimeter thereof.

TABLE V

| INGREDIENT | WEIGHT % |
|---|---|
| PHASE A | |
| Sodium Bicarbonate | 29.5 |
| Citraconic Acid (Anhydrous) | 45.4 |

TABLE V-continued

| INGREDIENT | WEIGHT % |
|---|---|
| Methyl Glucamide | 11.6 |
| Sodium Sesquicarbonate | 5.0 |
| Lipothix 100B ® (Potassium Polymetaphosphate/Bicarbonate 70:30) | 0.5 |
| Optigel SH ® (Sodium Magnesium Silicate) | 1.0 |
| Kelacid ® (Alginic Acid) | 1.0 |
| Sorbitol | 5.0 |
| PHASE B | |
| Fragrance | 0.9 |
| Yarrow | 0.1 |

The foregoing description and examples illustrate selected embodiments of the present invention. In light thereof variations and modifications will be suggested to one skilled in the art, all of which are within the spirit and purview of this invention.

What is claimed is:

1. A cosmetic article for cleansing body surfaces, the article comprising:

a sealed pouch formed with at least one water permeable wall; and an effervescent cleanser composition in an anhydrous dry solid form positioned within the pouch, the composition comprising from about 0.1 to about 3% by weight of the solid of a fragrance or botanical extract deposited upon the anhydrous dry solid and from about 0.01 to about 30% by weight of the solid of an anti-aging active selected from the group consisting of vitamins, retinoids and mixtures thereof.

2. A method for imparting a pleasant sensory feel to skin comprising wetting with water a cosmetic cleansing article, generating foam from the article and wiping skin surfaces with the wetted article, the article comprising:

a sealed pouch formed with at least one water permeable wall; and an effervescent cleanser composition in an anhydrous dry solid form positioned within the pouch, the composition comprising from about 0.1 to about 3% by weight of the solid of a fragrance or botanical extract deposited upon the anhydrous dry solid.

3. A cosmetic article for cleansing body surfaces, the article comprising a sealed pillow plumped by effervescent generated carbon dioxide and exuding lather and an emollient.

4. The article according to claim 3 wherein the effervescent generated carbon dioxide, the exuded lather and the emollient arise from a composition stored withing the pillow comprising from about 1 to about 80% of an alkaline material, from about 0.5 to about 80% of an acid material, from about 0.1 to about 30% of a surfactant and from about 0.01 to about 30% of an emollient by weight of the composition.

* * * * *